US012773382B2

(12) United States Patent
Wakizaka et al.

(10) Patent No.: US 12,773,382 B2
(45) **Date of Patent: *Oct. 27, 2026**

(54) BIOFILM REMOVER AND BIOFILM REMOVAL METHOD

(71) Applicant: SARAYA CO., LTD., Osaka (JP)

(72) Inventors: Miyako Wakizaka, Kashiwara (JP); Yoriko Kato, Kashiwara (JP); Yoshifumi Jahana, Kashiwara (JP); Hirotomo Komori, Kashiwara (JP); Yuka Oda, Kashiwara (JP); Yoshihiko Hirata, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 206 days.

This patent is subject to a terminal disclaimer.

(21) Appl. No.: 18/568,602

(22) PCT Filed: Jun. 8, 2022

(86) PCT No.: PCT/JP2022/023146

§ 371 (c)(1),
(2) Date: Dec. 28, 2023

(87) PCT Pub. No.: WO2022/260090

PCT Pub. Date: Dec. 15, 2022

(65) Prior Publication Data

US 2025/0120901 A1 Apr. 17, 2025

(30) Foreign Application Priority Data

Jun. 8, 2021 (JP) ................................ 2021-096114

(51) Int. Cl.
*A61K 8/60* (2006.01)
*A61K 8/04* (2006.01)
(Continued)

(52) U.S. Cl.
CPC .............. *A61K 8/602* (2013.01); *A61K 8/046* (2013.01); *A61K 8/19* (2013.01); *A61K 8/22* (2013.01);
(Continued)

(58) Field of Classification Search
CPC .......... A61K 8/602; A61K 8/046; A61K 8/19; A61K 8/22; A61K 9/0007; A61K 31/7032;
(Continued)

(56) References Cited

U.S. PATENT DOCUMENTS 9,271,908 B2 3/2016 Allef et al.
10,287,615 B2 5/2019 Develter et al.
(Continued)

FOREIGN PATENT DOCUMENTS

CN 109628076 A 4/2019
CN 109705990 A 5/2019
(Continued)

OTHER PUBLICATIONS

U.S. Appl. No. 17/789,454, filed Jun. 27, 2022.
(Continued)

*Primary Examiner* — Jianfeng Song
(74) *Attorney, Agent, or Firm* — Leydig, Voit & Mayer, Ltd.

(57) ABSTRACT

The biofilm remover of the present invention comprises a combination of the following components (A), (B) and (C):
(A) a sophorolipid containing acidic sophorolipid and lactonic sophorolipid in a ratio of 78:22 to 100:0 (mass ratio);
(B) a free fatty acid or a salt thereof; and
(C) a gas generation component.

7 Claims, 1 Drawing Sheet

(51) Int. Cl.

| | |
|---|---|
| ***A61K 8/19*** | (2006.01) |
| ***A61K 8/22*** | (2006.01) |
| ***A61K 9/46*** | (2006.01) |
| ***A61K 31/7032*** | (2006.01) |
| ***A61K 33/40*** | (2006.01) |
| ***A61K 47/02*** | (2006.01) |
| ***A61Q 17/00*** | (2006.01) |
| ***A61Q 19/10*** | (2006.01) |

(52) U.S. Cl.
CPC ........ *A61K 9/0007* (2013.01); *A61K 31/7032* (2013.01); *A61K 33/40* (2013.01); *A61K 47/02* (2013.01); *A61Q 17/005* (2013.01); *A61Q 19/10* (2013.01); *A61K 2800/85* (2013.01)

(58) Field of Classification Search
CPC .... A61K 33/40; A61K 47/02; A61K 2800/85; A61Q 17/005; A61Q 19/10
See application file for complete search history.

(56) References Cited

U.S. PATENT DOCUMENTS

| | | | | |
|---|---|---|---|---|
| 11,572,578 B2 | 2/2023 | Kato et al. | | |
| 2015/0010604 A1 | 1/2015 | Ishii et al. | | |
| 2018/0023040 A1* | 1/2018 | Schilling | .................. | C11D 1/83 510/392 |
| 2018/0044613 A1* | 2/2018 | Meier | ...................... | C11D 1/66 |
| 2019/0329199 A1 | 10/2019 | Sugano et al. | | |
| 2020/0375802 A1 | 12/2020 | Metcalf et al. | | |
| 2021/0262002 A1 | 8/2021 | Kato et al. | | |
| 2023/0056021 A1 | 2/2023 | Jahana et al. | | |

FOREIGN PATENT DOCUMENTS

| | | | | |
|---|---|---|---|---|
| CN | 110382676 A | 10/2019 | | |
| EP | 3594318 A1 * | 1/2020 | ......... | C11D 17/0043 |
| JP | 2013-049036 A | 3/2013 | | |
| JP | 2013-180956 A | 9/2013 | | |
| JP | 2015-071550 A | 4/2015 | | |
| JP | 2016-123925 A | 7/2016 | | |
| JP | 2016-160244 A | 9/2016 | | |
| JP | 2016-160264 A | 9/2016 | | |
| JP | 2017-087128 A | 5/2017 | | |
| JP | 2018-164898 A | 10/2018 | | |
| JP | 2019-214536 A | 12/2019 | | |
| WO | WO 2018/097019 A1 | 5/2018 | | |
| WO | WO 2020/027192 A1 | 2/2020 | | |
| WO | WO 2021/132701 A1 | 7/2021 | | |

OTHER PUBLICATIONS

Arai, "The Accelerating Industrialization of Fine Bubble Technology," *ARC Report* RS-1007 (2016) [https://arc.asahi-kasei.co.jp/report/arc_report/pdf/rs-1007.pdf].

Leaper et al., "Extending the TIME concept: what have we learned in the past 10 years?" *Intl. Wound J.*, 9(Suppl 2): 1-19 (2012).

Lydon et al., "Adjuvant Antibiotic Activity of Acidic Sophorolipids with Potential for Facilitating Wound Healing," *Antimicob. Agents Chemother.*, 61(5): e02547-16 (2017).

Meng et al., "Inhibition of Ethylenediaminetetraacetic acid (EDTA) on Biofilm Formation of *Staphylococcus aureus," Food Sci. Technol. Res.*, 19(2): 323-330 (2013).

Nakagami et al., "Innovation of Wound Care by Visualizing Biofilms," *Japanese Journal of Foot Care*, 16(1): 1-6 (2018).

Nakagami et al., "Visualizing Biofilms," *Visual Dermatology*, 17(2): 156-159 (2018).

Nakagami, "New Wound Care Utilizing Biofilm Detection Technology That Can Be Performed at the Bedside," *JSWH News Letter*, No. 105 (2018).

Schultz et al., "Consensus Guidelines for the Identification and Treatment of Biofilms in Chronic Nonhealing Wounds," *Wound Rep. Reg.*, 25(5): 744-757 (2017).

Shiroodi et al., "Efficacy of Nanobubbles Alone or in Combination with Neutral Electrolyzed Water in Removing *Escherichia coli* O157:H7, Vibrio parahaemolyticus, and *Listeria innocua* Biofilms," *Food and Process Technology*, 14: 287-297 (2021).

The Japanese Society of Pressure Ulcers, *Revised DESIGN-R®2020 Consensus Document* (2020).

Wolcott et al., "Biofilm Maturity Studies Indicate Sharp Debridement Opens a Time-Dependent Therapeutic Window," *J. Wound Care*, 19(8): 320-328 (2010).

Yamada et al., "Effect of Ultrafine Bubbles on *Pseudomonas aeruginosa* and *Staphylococcus aureus* During Sterilization of Machining Fluid," *Int. J. Automation Technology*, 15(1): 99-108 (2021).

Japan Patent Office, International Search Report in International Patent Application PCT/JP2020/049043 (Mar. 16, 2021).

China National Intellectual Property Administration, Office Action in Chinese Patent Application No. 202080097126.9 (Aug. 31, 2023).

Japan Patent Office, International Search Report in International Patent Application No. PCT/JP2022/023146 (Aug. 30, 2022).

European Patent Office, Extended European Search Report in European Patent Application No. 22820269.3 (May 16, 2025).

* cited by examiner

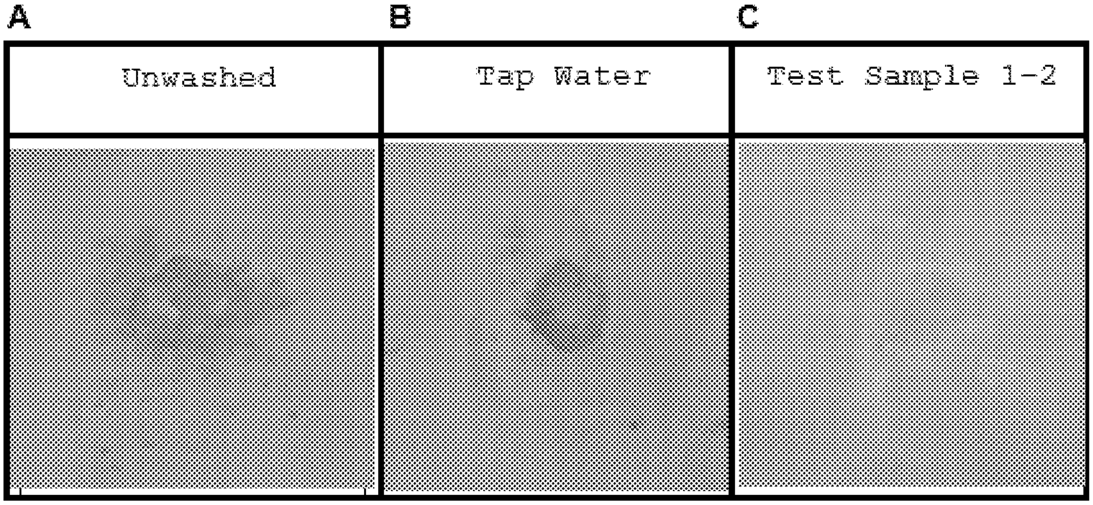
A
B
C
Unwashed
Tap Water
Test Sample 1-2

BIOFILM REMOVER AND BIOFILM REMOVAL METHOD

TECHNICAL FIELD

The present invention relates to a biofilm remover and a biofilm removal method using the biofilm remover.

BACKGROUND ART

Chronic wounds, such as pressure ulcers and diabetic foot ulcers, have an extremely high risk of developing infections because the wounds are constantly exposed to external bacteria and the host's immunity is weakened. In recent years, it has become clear that bacterial biofilms are involved in the pathophysiology of chronic wounds. Biofilm-based wound management, which is management of wounds depending on whether a biofilm is present or not, is considered important.

A biofilm is a community formed by the colonization of microorganisms, and its main constituents are glycoproteins, proteins, extracellular DNA, etc. A biofilm is present as a reservoir of bacteria and expresses pathogenicity by forming a population. Further, a biofilm can evade the effects of antibacterial agents and host immunity, causing chronic inflammation and becoming a very strong source of infection (see Non-Patent Literature (NPL) 1). Therefore, healing cannot be expected as long as a biofilm is present at the bottom of the wound. For this reason, it has been advocated since the latter half of the first decade of the 2000s that as biofilm-based wound therapy, wound treatment should be selected depending on whether a biofilm is present or not. Specifically, the international guidelines jointly published by the European, U.S., and Pan Pacific Pressure Ulcer Advisory Panel (EPUAP-NPUAP-PPPIA) in 2014 include the section "Assessment and treatment of infection and biofilms," in which the management method is explained. The guidelines recommend considering the possibility of whether biofilm may be present when, for example, the wound has been present for 4 weeks or more, there are no signs of healing for the past 2 weeks, there are findings of inflammation, or there is resistance to antibiotics. However, implementation in clinical practice is difficult because a definitive diagnosis of the presence of a biofilm requires tissue biopsy and microscopic observation (see NPL 1 above).

Therefore, there have recently been proposed technologies for quickly visualizing the distribution of a biofilm on the wound surface by detecting polysaccharide components, which are constituents of a biofilm, by application of wound blotting, which is a method for detecting a trace of components present on the wound surface (e.g., NPL 2 to NPL 4 and Patent Literature (PTL) 1).

Specifically, NPL 2 to NPL 4 disclose a method for visualizing a biofilm, the method comprising washing the wound surface, then applying a nitrocellulose membrane to the wound surface for 10 seconds, and then immersing the membrane in a staining solution (ruthenium red or Alcian blue) specific for a polysaccharide component derived from the biofilm. PTL 1 further discloses an improved method of the above technique and a biofilm detection reagent kit. This method comprises applying a sterilized membrane sheet to a wound site for 10 seconds and treating the sheet with a special pre-treatment solution, staining solution, and/or decolorant solution for a total of 2 minutes. To what extent and in which part a biofilm is formed on the wound surface can be visualized by performing such treatments. Further, this method is also considered to be useful in predicting necrotic formation and wound healing, as well as understanding critical colonization. "Critical colonization" is a growth state of a microorganism that is not invasive but inhibits wound healing. In other words, the non-sterile status at a wound site is between contamination or colonization, which does not affect wound healing, and infection, which shows obvious signs of infection and causes wound deterioration and healing stagnation, and this status is generally known as critical colonization (NPL 5).

These methods have recently allowed for easy, quick, and non-invasive, bed-side detection of a biofilm and enabled more appropriate management of the wound site.

On the other hand, debridement is one of the therapeutic practices for skin wounds. Debridement is a therapeutic practice for cleaning by removing dead tissues, aging cells that no longer respond to the stimulation of wound healing promotion factors such as growth factors, foreign matter, and bacterial infection foci that often accompany these. Debridement is useful for removing a biofilm formed at a wound site, a peri-wound site, etc. Repeating debridement can inhibit biofilm development and keep a biofilm weakened. However, although debridement is effective in reducing a biofilm, not all the microorganisms that are present at the wound site can be thereby removed. Therefore, it has been pointed out that the residual bacteria grow and form a biofilm again (NPL 6). Specifically, NPL 7 reports that tissues excised 24 hours after the debridement of a venous leg ulcer wound showed an antibiotic effect, whereas tissues excised 72 hours after debridement showed no antibiotic effect and were resistant to antibiotics. Further, NPL 8 reports that when a test cell solution was inoculated and statically cultured, the removal effect of a pharmaceutical agent on the biofilm cultured for 12 hours was higher than that on the biofilm cultured for 72 hours. NPL 8 speculates that when the test cell solution was cultured for 72 hours, the biofilm matured and became resistant to antibiotics.

Further, since conventional surgical debridement using a scalpel is highly invasive, repeating debridement imposes the problem of a significant burden on the patient. Therefore, in recent years, methods using high-pressure water flow and ultrasound have been attracting attention. However, these methods have problems in that the equipment is expensive and only doctors or doctor-supervised nurses can implement such methods.

As a minimally invasive method, PTL 2 proposes a wound treatment method comprising allowing fine bubbles to act on a wound site to wash the wound site. This method is a method for washing a wound site by using a washing device comprising a washing container containing a gas solution obtained by dissolving a target gas for forming fine bubbles in a solvent, the device being configured to generate fine bubbles in the gas solution when the pressure applied to the gas solution is reduced and/or the temperature of the gas solution is raised. Further, as a biofilm removal method without using any device, PTL 3 proposes a method comprising applying a biofilm remover in the form of a gel to a test site, the biofilm remover containing water and at least one member selected from the group consisting of potassium oleate and sodium oleate in a specific amount, and then washing with water. This method can remove a biofilm at a removal rate of 88.7 to 90.3% and is considered to impose less of a burden on the human body.

CITATION LIST

Patent Literature

PTL 1: WO2020/027192
PTL 2: JP2018-164898A
PTL 3: JP2019-214536A

Non-Patent Literature

NPL 1: David J Leaper et al., Extending the TIME concept: What have we learned in the past 10 years?International Wound Journal 2012; 9 (Suppl. 2): pp. 1-19 (in particular, pages 6-7)

NPL 2: Gojiro Nakagami et al., Transformation of wound care with biofilm visualization, Journal of the Japanese Society of Footcare, 2018: 16(1); pp. 1-6

NPL 3: Gojiro Nakagami et al., Visualize biofilm, Visual Dermatology Vol. 17, No. 2, 2018; pp. 156-159

NPL 4: Gojiro Nakagami, New wound care utilizing biofilm detection technology that can be performed at the bedside, JSWH News Letter, May 2018; No. 105

NPL 5: Japan Society of Pressure Ulcers, Pressure Ulcer Condition Rating Scale, Revised DESIGN-® (registered trademark) 2020 Consensus Document, Shorinsha Inc., 2020 (in particular, pages 26-29 before the section "Notation System in DESIGN-R (registered trademark) 2020")

NPL 6: Gregory Schultz et al., Consensus guidelines for the identification and treatment of biofilms in chronic non-healing wounds, Wound Repair and Regeneration, 2017, 25(5), pp. 744-757

NPL 7: R. D. Wolcott et al., Biofilm maturity studies indicate sharp debridement opens a time-dependent therapeutic window, Journal of Wound Care, 2010, 19(8), pp. 320-328

NPL 8: Liangyu Meng et al., Inhibition of Ethylenediaminetetraacetic acid (EDTA) on Biofilm Formation of *Staphylococcus aureus*, Food Sci. Technol. Res., 2013: 19(2); pp. 323-330

SUMMARY OF INVENTION

Technical Problem

An object of the present invention is to provide a biofilm remover and a biofilm removal method using the biofilm remover. Specifically, an object of the present invention is to provide a biofilm remover that has a high degree of a biofilm removal effect and that imposes less of a burden on the human body and is highly safe due to its low cytotoxicity, and to provide a biofilm removal method using the biofilm remover.

Solution to Problem

The present inventors conducted extensive research to solve the above problem. As a result, the inventors found that when (A) a sophorolipid containing acidic sophorolipid and lactonic sophorolipid in a mass ratio of 78:22 to 100:0, (B) a free fatty acid or a salt thereof, and (C) a gas generation component are allowed to all be present in water, fine bubbles, which correspond to ultrafine bubbles, can be generated without using any device. Further, the present inventors confirmed that the solution containing the fine bubbles has an excellent biofilm removal effect. The present inventors further confirmed that the solution having the fine bubbles has low cytotoxicity and is highly safe to the living body and less invasive to the human body.

The present invention has been accomplished through further research based on the above findings. The present invention includes the following embodiments.

Below, "fine bubbles that correspond to ultrafine bubbles" may be abbreviated as "UFB," and "sophorolipid" may be abbreviated as "SL."

(I) Biofilm Remover (I-1) A biofilm remover comprising a combination of the following (A), (B), and (C):

(A) an SL containing acidic SL and lactonic SL in a ratio of 78:22 to 100:0 (mass ratio);

(B) a free fatty acid or a salt thereof; and (C) a gas generation component.

(I-2) The biofilm remover according to (I-1), wherein (C) is at least one member selected from the group consisting of a carbon dioxide gas (referred to below as "$CO_2$ gas") generation component, a hydrogen gas (referred to below as "$H_2$ gas") generation component, and an oxygen gas (referred to below as "$O_2$ gas") generation component.

(I-3) The biofilm remover according to (I-2), wherein the $CO_2$ gas generation component is a carbonate or a hydrogen carbonate, or a combination of a carbonate or a hydrogen carbonate with a counterpart corresponding thereto;

the $H_2$ gas generation component is a hydride, a borohydride, or hydrochloric acid, or a combination of a hydride, a borohydride, or hydrochloric acid with a counterpart corresponding thereto; and the $O_2$ gas generation component is hydrogen peroxide or a combination of hydrogen peroxide with its counterpart.

(I-4) The biofilm remover according to any one of (I-1) to (I-3), which is a composition of (A), (B), and (C) or a product combination in which at least (C) is packaged separately from (A) and (B).

(I-5) The biofilm remover according to any one of (I-1) to (I-4), further comprising (D) water with a hardness of 30 to 200 mg/L, wherein at least (D) is packaged separately from (A), (B), and (C).

(II) Method for Using the Biofilm Remover (II-1) A method for using the biofilm remover of any one of (I-1) to (I-5), the method comprising (1) adding the biofilm remover of any one of (I-1) to (I-4) to water with a hardness of 30 to 200 mg/L to prepare a biofilm removal solution so that the concentrations of (A), (B) and (C) in the water fall within the following ranges:

when (C) is a $CO_2$ gas generation component, the concentration of (A) is 0.008 to 0.09 mass %, the concentration of (B) is 0.0006 to 0.0065 mass %, and the concentration of (C) in terms of gas generator is 0.09 to 0.882 mass %;

when (C) is a $H_2$ gas generation component, the concentration of (A) is 0.00009 to 0.1 mass %;

the concentration of (B) is 0.00001 to 0.01 mass %; and the concentration of (C) in terms of gas generator is 0.001 to 0.9 mass %; and when (C) is an $O_2$ gas generation component, the concentration of (A) is 0.004 to 0.1 mass %, the concentration of (B) is 0.0005 to 0.02 mass %; and the concentration of (C) in terms of gas generator is 0.01 to 0.9 mass %; and (2) bringing the biofilm removal solution prepared in (1) into contact with a target site of a mammal, the target site having a biofilm formed or having a potential of having a biofilm formed. (II-2) The method according to (II-1), wherein the biofilm removal solution prepared in step (1) has fine bubbles with an average number particle size of less than 1,000 nm, the fine bubbles being formed of at least one gas selected from the group consisting of $CO_2$ gas, $H_2$ gas, and $O_2$ gas.

(III) Biofilm Removal Solution (III-1) A biofilm removal solution containing the following (A), (B), (c), and (d):

(A) an SL containing acidic SL and lactonic SL in a ratio of 78:22 to 100:0 (mass ratio), (B) a free fatty acid or a salt thereof, (c) fine bubbles with an average number particle size of less than 1,000 nm, the fine bubbles being formed of at least one gas selected from the group consisting of $CO_2$ gas, $H_2$ gas, and $O_2$ gas; and (d) water.

(III-2) The biofilm removal solution according to (III-1), wherein the concentrations of (A) and (B) are in the following ranges:

when (C) is a $CO_2$ generation component,
the concentration of (A) is 0.008 to 0.09 mass % and
the concentration of (B) is 0.0006 to 0.0065 mass %;
when (C) is a $H_2$ gas generation component,
the concentration of (A) is 0.00009 to 0.01 masse and
the concentration of (B) is 0.00001 to 0.01 mass %; and
when (C) is an oxygen gas generation component,
the concentration of (A) is 0.004 to 0.1 mass % and
the concentration of (B) is 0.0005 to 0.02 mass %.

(III-3) The biofilm removal solution according to (III-1) or (III-2), wherein (d) is water with a hardness of 30 to 200 mg/L.

(IV) Method for Preparing Biofilm Removal Solution (IV-1) A method for preparing a biofilm removal solution comprising adding the following components (A) to (C) to water with a hardness of 30 to 200 mg/L:

(A) an SL containing acidic SL and lactonic SL in a ratio of 78:22 to 100:0 (mass ratio);

(B) a free fatty acid or a salt thereof; and (C) a gas generation component; and allowing (A), (B), and (C) to all be present in water so that the concentrations of (A), (B), and (C) fall within the following concentrations:

when (C) is a $CO_2$ gas generation component,
the concentration of (A) is 0.008 to 0.09 mass %,
the concentration of (B) is 0.0006 to 0.0065 mass %, and
the concentration of (C) in terms of gas generator is 0.09 to 0.882 mass %;
when (C) is a $H_2$ gas generation component,
the concentration of (A) is 0.00009 to 0.1 mass %,
the concentration of (B) is 0.00001 to 0.01 mass %, and
the concentration of (C) in terms of gas generator is 0.001 to 0.9 mass %; and
when (C) is an $O_2$ gas generation component,
the concentration of (A) is 0.004 to 0.1 mass %,
the concentration of (B) is 0.0005 to 0.02 mass %, and
the concentration of (C) in terms of gas generator is 0.01 to 0.9 mass %.

(V) Biofilm Removal Method (V-1) A method for removing a biofilm from a target site (a site to be tested) of a mammal, the method comprising bringing the biofilm removal solution of any one of (III-1) to (III-3) into contact with the site to be tested, the target site having a biofilm formed or having a potential of having a biofilm formed.

(V-2) The biofilm removal method according to (V-1), wherein the site to be tested is a wound site, a peri-wound site, the oral cavity, or a skin surface other than the wound site or the peri-wound site.

(VI) Product Combination for Use in Removing a Biofilm (VI-1) A product combination for use in removing a biofilm, the combination comprising the following (A), (B), and (C):

(A) an SL containing acidic SL and lactonic SL in a ratio of 78:22 to 100:0 (mass ratio);

(B) a free fatty acid or a salt thereof; and (C) a gas generation component.

(VI-2) The product combination according to (VI-1), further comprising water with a hardness of 30 to 200 mg/L.

(VI-3) The product combination for use in removing a biofilm according to (VI-1) or (VI-2), wherein the product combination is prepared by adding (A), (B), and (C) to (D) water with a hardness of 30 to 200 mg/L so that the concentrations of (A), (B), and (C) fall within the following ranges:

when (C) is a $CO_2$ gas generation component,
the concentration of (A) is 0.008 to 0.09 mass %,
the concentration of (B) is 0.0006 to 0.0065 mass %, and
the concentration of (C) in terms of gas generator is 0.09 to 0.882 mass %;
when (C) is a $H_2$ gas generation component,
the concentration of (A) is 0.00009 to 0.1 mass %,
the concentration of (B) is 0.00001 to 0.01 mass %, and
the concentration of (C) in terms of gas generator is 0.001 to 0.9 mass %; and
when (C) is an $O_2$ gas generation component,
the concentration of (A) is 0.004 to 0.1 mass %,
the concentration of (B) is 0.0005 to 0.02 mass %, and
the concentration of (C) in terms of gas generator is 0.01 to 0.9 mass %.

(VII) Use in Producing Biofilm Removal Solution (VII-1) Use of a biofilm remover in producing a biofilm removal solution, the biofilm remover comprising a product combination of (A), (B) and (C):

(A) an SL containing acidic SL and lactonic SL in a ratio of 78:22 to 100:0 (mass ratio);

(B) a free fatty acid or a salt thereof; and (C) a gas generation component.

(VII-2) The use according to (VII-1), wherein the product combination further comprises (D) water with a hardness of 30 to 200 mg/L.

(VII-3) The use according to (VII-1) or (VII-2), wherein the biofilm remover is used to prepare a biofilm removal solution by adding (A) to (C) to (D) water with a hardness of 30 to 200 mg/L so that the concentrations of (A), (B), and (C) in the water fall within the following ranges and the biofilm removal solution is used for removing a biofilm:

when (C) is a $CO_2$ gas generation component, the concentration of (A) is 0.008 to 0.09 mass %, the concentration of (B) is 0.0006 to 0.0065 mass %, and the concentration of (C) in terms of gas generator is 0.09 to 0.882 mass %;

when (C) is a $H_2$ gas generation component, the concentration of (A) is 0.00009 to 0.1 mass %, the concentration of (B) is 0.00001 to 0.01 mass %, and the concentration of (C) in terms of gas generator is 0.001 to 0.9 mass %; and when (C) is a $O_2$ gas generation component, the concentration of (A) is 0.004 to 0.1 mass %, the concentration of (B) is 0.0005 to 0.02 mass %, and the concentration of (C) in terms of gas generator is 0.001 to 0.9 mass %.

Advantageous Effects of Invention

The biofilm remover of the present invention can generate bubbles in water without using a bubble generation device. The biofilm remover, which contains bubbles, can form a biofilm removal solution capable of effectively removing a biofilm.

In particular, the biofilm removal solution prepared from a biofilm remover so that the concentrations of (A) to (C) in water fall within specific ranges prescribed according to the type of generated bubbles (gas) can relatively stably retain fine bubbles with an average number particle size of less than 1,000 nm in a liquid. Therefore, due to the UFB, the biofilm itself or bacteria that cause biofilm formation can be removed for a relatively long period of time to thereby prevent biofilm formation.

Even when prepared to contain SL at a relatively low concentration, the biofilm removal solution of the present invention can effectively exhibit the above effect due to the action of bubbles, in particular, UFB. The biofilm removal solution, which has low cytotoxicity and has safety that is equivalent to or higher than the safety of physiological saline, has an effective biofilm removal effect and an effective effect of removing bacteria that cause biofilm formation.

BRIEF DESCRIPTION OF DRAWINGS

FIG. 1 shows the results of Example 5. A shows a stained image of an unwashed pig skin model. B shows a stained image of a pig skin model washed with tap water. C shows a stained image of a pig skin model over which a biofilm removal solution was sprayed (Test Sample 1-2).

DESCRIPTION OF EMBODIMENTS (1) Biofilm Remover

The biofilm remover of the present invention is characterized by comprising a combination of the following (A), (B), and (C):

(A) a sophorolipid containing acidic sophorolipid and lactonic sophorolipid in a ratio of 78:22 to 100:0 (mass ratio);

(B) a free fatty acid or a salt thereof; and (C) a gas generation component.

The biofilm remover of the present invention may be a combination of the above (A) to (C) with the following (D):

(D) water with a hardness of 30 to 200 mg/L.

(A) Sophorolipid (SL)

Sophorolipid (SL) is generally a glycolipid consisting of sophorose or a sophorose whose one or more hydroxy groups are acetylated or esterified, and a hydroxy fatty acid. Sophorose is a sugar consisting of two glucose molecules bound through a β1→2 bond. Hydroxy fatty acid is a fatty acid having a hydroxy group. SL is roughly classified into acidic SL and lactonic SL. Acidic SL is a sophorolipid in which the carboxy group of the hydroxy fatty acid is free. Lactonic SL is a sophorolipid in which the carboxy group of the hydroxy fatty acid is bound to the sophorose in the molecule. Examples of acidic SL include an SL represented by formula (1) below, and examples of lactonic SL include an SL represented by formula (2) below. The SL obtained from SL-producing yeast through fermentation is usually a mixture of acidic SL and lactonic SL, and is obtained as a collection of 30 or more types of structural homologues, such as those having different fatty acid chain lengths ($R_2$), those acetylated or protonated at the 6'-position ($R_3$) and the 6"-position ($R_4$) of the sophorose, and those esterified at one of the 3'-, 4'-, 2"-, 3"-, and 4"-positions ($R_5$) of the sophorose.

Acidic SL (1)

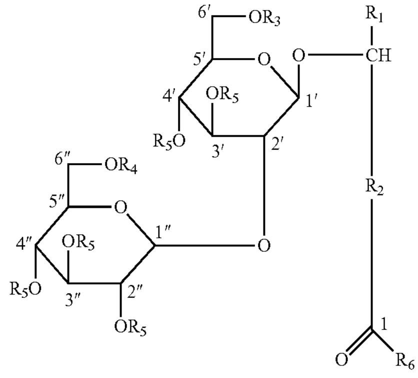

(In formula (1), $R_1$ represents a hydrogen atom or a methyl group;

$R_3$ and $R_4$ are the same or different and independently represent a hydrogen atom or an acetyl group;

all $R_5$ are hydrogen atoms, or one of the five $R_5$ is a saturated or unsaturated fatty acid residue that may have hydroxy, and the rest are all hydrogen atoms;

$R_2$ is a saturated aliphatic hydrocarbon chain, or an unsaturated aliphatic hydrocarbon chain having at least one double bond, which may have one or more substituents; and $R_6$ is a hydroxy group).

Lactonic SL (2)

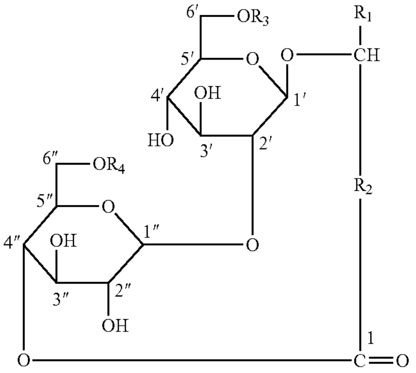

(In formula (2), $R_1$ to $R_4$ are as defined in formula (1)).

The SL targeted by the present invention may contain a dimer (dimeric SL) comprising an acidic SL represented by formula (1) wherein one $R_5$ is a saturated or unsaturated fatty acid residue that may have a hydroxyl group, the rest of four $R_5$ are a hydrogen atom, and $R_6$ at the C-1 position is bound to one of $R_7$ of an acidic SL represented by the following formula (3) below to form a single bond.

Dimeric SL (3)

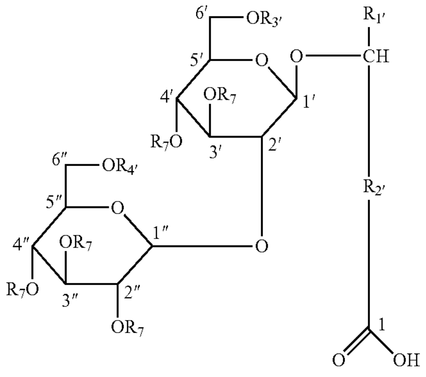

(In formula (3), $R_{1'}$ is a hydrogen atom or a methyl group;

$R_{3'}$ and $R_{4'}$ are the same or different and represent a hydrogen atom or an acetyl group;

$R_{2'}$ is a saturated aliphatic hydrocarbon chain or an unsaturated aliphatic hydrocarbon chain having at least one double bond and may have one or more substituents; and one $R_7$ is bound to $R_6$ of the acidic SL represented by formula (1) to form a single bond, and the rest of the $R_7$ are all hydrogen atoms.)

In formulas (1) to (3), the number of carbons in the saturated or unsaturated aliphatic hydrocarbon chain represented by $R_2$ or $R_2$' is not limited, but is usually 9 to 20, preferably 9 to 18, more preferably 11 to 16, and particularly preferably 14 to 16. The saturated aliphatic hydrocarbon chain can be, for example, a linear or branched chain alkylene group, and is preferably a linear alkylene group. Examples of the unsaturated aliphatic hydrocarbon chain include alkenylene groups having 1 to 3 double bonds. The unsaturated aliphatic hydrocarbon chain is preferably an alkenylene group having 1 to 2 double bonds, and more preferably an alkenylene group having 1 double bond. There is no limitation on the substituent of the saturated or unsaturated aliphatic hydrocarbon chain represented by $R_2$ or $R_2$'. Examples of substituents include halogen atoms, a hydroxy group, lower ($C_{1-6}$) alkyl groups, halo-lower ($C_{1-6}$) alkyl groups, hydroxy lower ($C_{1-6}$) alkyl groups, and halo-lower ($C_{1-6}$) alkoxy groups. Examples of halogen atoms or halogen atoms bound to alkyl or alkoxy groups include a fluorine atom, a chlorine atom, a bromine atom, and an iodine atom.

Examples of saturated fatty acid residues represented by $R_5$ in formula (1) include $C_{12-20}$ linear fatty acid residues (lauric acid residue, myristic acid residue, pentadecylic acid residue, palmitic acid residue, margaric acid residue, stearic acid residue, and arachidic acid residue), preferably $C_{14-20}$, more preferably $C_{16-20}$, even more preferably $C_{16-18}$ linear fatty acid residues, and particularly preferably $C_{16}$ palmitic acid residue and $C_{18}$ stearic acid residue. Examples of unsaturated fatty acid residues include $C_{12-20}$ linear fatty acid residues having 1 to 3 double bonds. The number of double bonds is preferably 1 to 2 and more preferably 1. The number of carbon atoms is preferably 16 to 20, more preferably 16 to 18, and particularly preferably 18. Preferable examples of unsaturated fatty acid residues include $C_{16}$ palmitoleic acid residue having one double bond; $C_{18}$ oleic acid residue or vaccenic acid residue having one double bond (preferably oleic acid residue); $C_{18}$ linoleic acid residue having two double bonds; $C_{18}$ linolenic acid residue (9,12,15), linolenic acid residue (6,9,12), and eleostearic acid residue each having three double bonds; and $C_{20}$ linolenic acid residue (9,12,15), linolenic acid residue (6,9, 12), and eleostearic acid residue each having two double bonds; more preferably Cc palmitoleic acid residue having one double bond and $C_{18}$ oleic acid residue having one double bond; and particularly preferably $C_{18}$ oleic acid residue having one double bond.

These fatty acid residues may have hydroxy or may not have hydroxy. When the fatty acid residues have hydroxy, the number of hydroxy groups is 1 or 2, and preferably 1. The hydroxy may be present, for example, at the ω-position or ω-1-position in the fatty acid residue. In acidic SL (1), when $R_5$ is a saturated or unsaturated fatty acid residue that may have hydroxy, —$OR_5$ may be present at any of the 3', 4', 2", 3", and 4"-positions of the sophorose ring. More specifically, acidic SL (1) includes an SL compound in which an —$OR_5$ group having $R_5$ that is the fatty acid residue described above is present at one of these positions. More preferably, acidic SL (1) is a compound (1) in which —$OR_5$ having $R_5$ that is a saturated or unsaturated fatty acid residue that may have hydroxy is present at the 4"-position of the sophorose ring.

As described above, in a liquid culture obtained through fermentation by an SL-producing yeast, SL is usually present as a mixture of acidic SL (monomeric SL shown in formula (1)) and lactonic SL (monomeric SL shown in formula (2)). Among these, since the lactonic SL is a nonionic oily substance and is extremely insoluble in water by itself, it is undesirable to have lactonic SL in a high ratio because it causes a sophorolipid mixture to be water-insoluble as a whole. On the other hand, it is preferable to have acidic SL in a high ratio because it is chemically stable as compared to lactonic SL.

Examples of preferable SL-producing yeast include *Candida bombicola*. The *Candida* genus has been renamed the *Starmerella* genus. This yeast is SL-producing yeast known to produce a significant amount of (acidic and lactonic) SL (Canadian Journal of Chemistry, 39, 846 (1961) (note: the *Torulopsis* genus described in the document belongs to the *Candida* genus, but is currently classified into the *Starmerella* genus, as described above); Applied and Environmental Microbiology, 47, 173 (1984); etc.). *Candida* (*Starmerella*) *bombicola* has been deposited with, and is available from, the American Type Culture Collection (ATCC), which is a bioresource bank (e.g., *Candida bombicola* ATCC22214). Other SL-producing yeast that belongs to the *Candida* genus (*Starmerella* genus) and is known to produce (acidic and lactonic) SL can also be used. Examples of such SL-producing yeast include *Candida magnoliae, Candida gropengisseri, Candida apicola, Candida petrophilum, Candida bogoriensis*, and *Candida batistae.*

The culture of such SL-producing yeast uses a culture medium containing, as carbon sources, a sugar such as glucose (hydrophilic substrate), and fatty acid, a fatty acid ester such as fatty acid triglyceride, or oil and fat such as vegetable oil containing fatty acid as a component (hydrophobic substrate). Other components of the culture medium are not particularly limited and can be suitably selected from medium components generally used for yeast.

The SL used in the present invention refers to a composition in which acidic SL represented by formula (1) is present in a proportion of 78 mass % or more, and lactonic SL represented by formula (2) is present in a proportion of 22 mass % or less, based on the total amount (100 mass %) of the acidic SL and lactonic SL; preferably a composition in which acidic SL is present in a proportion of 85 mass % or more and lactonic SL is present in a proportion of 15 mass % or less; more preferably a composition in which acidic SL is present in a proportion of 90 mass % or more and lactonic SL is present in a proportion of 10 mass % or less; and even more preferably a composition in which acidic SL is present in a proportion of 95 mass % or more and lactonic SL is present in a proportion of 5 mass % or less. The SL may be an SL free of lactonic SL, specifically, an SL in which the proportion of acidic SL is 100 mass %.

The ratio of acidic SL to lactonic SL in the SL-containing composition in, for example, an SL-producing yeast culture or its processed product, can be determined by the measurement method described, for example, in WO2015/020114, the contents of which are hereby incorporated by reference. Specifically, the following method can be used: a solution prepared by mixing a mixture of acidic SL and lactonic SL (SL-containing composition) with an equal volume of a 50 volume % aqueous ethanol solution is subjected to reversed-phase column chromatography as described below, and the obtained fractions are further subjected to high-performance liquid chromatography (HPLC) to quantitatively analyze the SL content of each elution fraction.

Fractionation by Reversed-Phase Column Chromatography (1) A solution obtained by mixing 600 g of an SL-containing composition and an equal volume of a 50 volume % aqueous ethanol solution is subjected to reversed-phase column chromatography under the following conditions.

Solid phase: $C_{18}$ column (Cosmosil 40C18-PREP, produced by Nacalai Tesque, Inc., 7.5 kg)

Mobile phase: an aqueous ethanol solution having an ethanol concentration of 50 to 95 volume %

(2) Specifically, 10 L of a 50 volume % aqueous ethanol solution, 10 L of a 80 volume % aqueous ethanol solution, 15 L of a 90 volume % aqueous ethanol solution, and 15 L of a 95 volume % aqueous ethanol solution are sequentially subjected to the solid phase, and the fractions eluted with the 80 volume % aqueous ethanol solution, the 90 volume % aqueous ethanol solution, and the 95 volume % aqueous ethanol solution are collected.

(3) Each elution fraction is evaporated to dryness and then dissolved in ethanol. These solutions are used as test samples and subjected to HPLC under the following conditions.

Quantitative Analysis by HPLC

Conditions

Device: Shimadzu Corporation LC-10 AD-VP

Column: Inertsil ODS-3 (4.6 mm×250 mm)

Column temperature: 40° C.

Mobile phase: [A] distilled water,

[B] Methanol containing 0.1 volume % formic acid

Gradients: 0 min→60 min: [B]70→100 volume %

60 min→70 min: [B]100→70 volume %.

Flow rate: 1.0 mL/min

Sample injection volume: 10 μL

Detector: Evaporative light scattering detector (ELSD-LTII, produced by Shimadzu Corporation)

Detector temperature: 40° C.

Gain: 5

Gas pressure: 350 kpa ($N_2$ gas)

The fraction eluted with the 80 volume % aqueous ethanol solution contains acidic SL represented by the following formula (1a) among acidic SLs represented by formula (1). Among acidic SLs represented by formula (1), this type of acidic SL is an acidic SL represented by formula (1) in which all $R_5$ are a hydrogen atom. In the HPLC under the above conditions, the acidic SL (1a) elutes in a retention time zone of 10 to 25 minutes.

(1a)

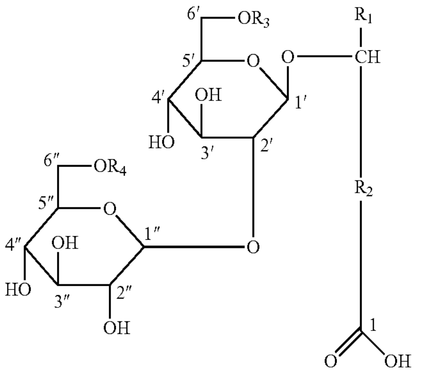

(In formula (1a), $R_1$ to $R_4$ are the same as defined in formula (1).)

The fraction eluted with the 80 volume % aqueous ethanol solution contains not only the acidic SL (1a) but also the lactonic SL represented by formula (2) above. In the HPLC under the above conditions, the lactonic SL (2) elutes in a retention time zone of 25 to 40 minutes.

The fraction eluted with the 90 volume % aqueous ethanol solution contains acidic SL (1b), which is one of the acidic SLs represented by formula (1) wherein one $R_5$ is a saturated or unsaturated fatty acid residue that may have a hydroxy group and the rest of the $R_5$ are a hydrogen atom. In the HPLC under the above conditions, the acidic SL (1b) elutes in a retention time zone of 45 to 60 minutes.

The fraction eluted with the 95 volume % aqueous ethanol solution contains dimeric SL represented by formula (3). In HPLC under the above conditions, the dimeric SL (3) elutes in a retention time zone of 60 to 70 minutes.

Thus, the ratio of acidic SL and lactonic SL contained in the SL-containing composition, specifically, the ratio of acidic SL and ratio of lactonic SL based on the total amount (100 mass %) of acidic SL and lactonic SL can be determined from the area ratio of the peaks detected in each retention time zone in HPLC under the above conditions.

The SL in the present invention is not particularly limited in form and may be in the form of a liquid, an emulsion, or a solid. Examples of the solid form include dry solids, such as freeze-dried products, spray-dried products, and evaporated dried products; tablets; pills; powders; granules; and capsules. The ratio of SLs in the biofilm remover can be suitably selected from the range of 1 to 80 mass % based on the total amount (100 mass %) of components (A), (B), and (C) as long as the effect of the present invention can be attained.

(B) Free Fatty Acid or Salt Thereof

The free fatty acid, which is a target in the present invention, may be saturated or unsaturated fatty acid as long as the effects of the present invention can be achieved. Examples of saturated fatty acids include $C_{12-20}$ fatty acids (lauric acid, myristic acid, pentadecylic acid, palmitic acid, margaric acid, stearic acid, and arachidic acid), preferably $C_{14-20}$, more preferably $C_{16-20}$, even more preferably $C_{16-18}$ fatty acids, and particularly preferably $C_{16}$ palmitic acid. Examples of unsaturated fatty acids include $C_{12-20}$ fatty acids having 1 to 3 double bonds. The number of double bonds is preferably 1 to 2 and more preferably 1. The number of carbon atoms is preferably 16 to 20, more preferably 16 to 18, and particularly preferably 18. Preferable examples of unsaturated fatty acids include $C_{16}$ palmitoleic acid having one double bond; $C_{18}$ oleic acid or vaccenic acid having one double bond (preferably oleic acid); $C_8$ linoleic acid having two double bonds; $C_{18}$ linolenic acid (9,12,15), linolenic acid (6,9,12), and eleostearic acid each having three double bonds; and $C_{20}$ linolenic acid (9,12,15), linolenic acid (6,9,12), and eleostearic acid each having two double bonds. More preferably, the unsaturated fatty acid is $C_{16}$ palmitoleic acid having one double bond or $C_{18}$ oleic acid, and particularly preferably oleic acid.

The salts of these fatty acids are not particularly limited as long as they do not impair the effects of the present invention. The salts of these fatty acids are preferably those that do not impair the solubility of free fatty acid in water. Specific examples include salts of alkali metals, such as sodium and potassium, and salts of alkaline earth metals, such as calcium and magnesium, and preferably alkali metal salts.

The free fatty acid or a salt thereof in the present invention is not particularly limited in form, and may be in the form of a liquid, an emulsion, or a solid. Examples of the solid form include dry solids, tablets, pills, powders, granules, and capsules. The ratio of component (B) in the biofilm remover of the present invention can be suitably selected from the range of 0.0001 to 19.9 mass % based on the total amount (100 mass %) of components (A), (B), and (C) as long as the effect of the present invention can be achieved.

(C) Gas Generation Component

The gas generation component, which is a target in the present invention, is a component that reacts in the presence of water to generate gas. As long as the gas generation component is a component that reacts in the presence of water to generate gas, it may consist of a single component or a combination of two or more components. The gas generation component may comprise a combination of a gas generator and its counterpart, as described below.

Examples of the target gas include, but are not limited to, $CO_2$ gas, $H_2$ gas, and $O_2$ gas. The target gas is preferably $CO_2$ gas.

The $CO_2$ gas generation component can be any component that reacts in the presence of water to generate $CO_2$ gas (carbon acid gas). Examples include carbonates or hydrogen carbonates. When a carbonate or hydrogen carbonate is placed in an aqueous solution containing component (A), carbon acid gas is generated. Preferable examples of carbonates include alkali metal salts, such as sodium carbonate and potassium carbonate. Preferable examples of hydrogen carbonates include alkali metal salts, such as sodium hydrogen carbonate and potassium hydrogen carbonate.

The carbonate or hydrogen carbonate can also be used in combination with a component that decomposes the carbonate or hydrogen carbonate in the presence of water to generate carbon acid gas. In the present invention, a component that decomposes a gas generator, such as a carbonate, or a component that contributes to gas generation by promoting the decomposition of the gas generator is referred to as a "counterpart" as a component that is used in combination with the gas generator. Examples of the counterpart that is used in combination with the carbonate or hydrogen carbonate (gas generator) include acids and acid salts.

The acid used herein may be any acid that reacts with a carbonate or hydrogen carbonate in the presence of water to generate carbon acid gas, and that does not impair the effects of the present invention. Examples include inorganic acids, such as hydrochloric acid and sulfuric acid; and organic acids, such as succinic acid, fumaric acid, adipic acid, tartaric acid, benzoic acid, citric acid, pyrrolidonic carboxylic acid, salicylic acid, maleic acid, phthalic acid, glutaric acid, and oxalic acid. These acids can be used singly or in a combination of two or more. Preferable examples of acid salts include salts with alkali metal, such as sodium and potassium.

The $H_2$ gas generation component can be any component that reacts in the presence of water to generate $H_2$ gas. Examples of $H_2$ gas generators include hydrides, borohydrides, and hydrochloric acid. The hydrides or borohydrides can be any salts as long as the salts exert the above effects. Examples include salts of alkali metals, such as sodium and potassium, and salts of alkaline earth metals, such as calcium and magnesium. Specifically, examples of hydrides include sodium hydride, potassium hydride, calcium hydride, and magnesium hydride. Examples of borohydrides include sodium borohydride.

Among the $H_2$ gas generation components, hydrochloric acid can also be used in combination with a component (counterpart) that decomposes hydrochloric acid in the presence of water to generate hydrogen gas. Examples of the counterpart that is used in combination with hydrochloric acid include metals, such as iron, zinc, or magnesium.

The $O_2$ gas generation component can be any component that reacts in the presence of water to generate $O_2$ gas. Examples of $O_2$ gas generators include hydrogen peroxide. Hydrogen peroxide can also be used in combination with a component (counterpart) that decomposes hydrogen peroxide in the presence of water to generate $O_2$ gas. Examples of the counterpart used in combination with hydrogen peroxide include hydrogen peroxide degradation enzymes, such as catalase, and catalysts, such as manganese dioxide.

In the biofilm remover of the present invention, the form of the gas generation component is not particularly limited as long as the gas generation component is configured to generate gas for the first time when it is in contact with water. The gas generation product is preferably in the form of a solid. Examples of the solid form include dry solids, tablets, pills, powders, granules, and capsules. As mentioned above, the gas generation component may be used in combination with the gas generator and its counterpart. In this case it is preferable to combine the gas generator and its counterpart in a separated state so that the reaction occurs only when they come into contact with water. The ratio of component (C) in the biofilm remover of the present invention may be suitably selected from a range of 0.1 to 98.9999 mass % per 100 mass % of the total of components (A), (B), and (C) as long as the effects of the present invention can be attained.

(D) Water with a Hardness of 30 to 200 mg/L

The water is used to dissolve (A) to (C) described above. When (A) to (C) are added to the water, gas (bubbles), preferably UFB, is generated in the water. The water preferably has a hardness in the range of 50 to 200 mg/L. As long as the water has a hardness within the range described above and generation of bubbles, in particular, UFB, is not impaired, any optional component can also be incorporated (for example, an aqueous solution containing an optional component).

The hardness (mg/L) means American hardness (or Japanese hardness). Specifically, the hardness can be determined by calculating the amounts of calcium and magnesium in terms of calcium carbonate ($CaCO_3$) according to equation 1 below.

$$\text{Hardness}\,[\text{mg/l}] = (\text{Amount of calcium}\,[\text{mg/l}] \times 2.5) + (\text{Amount of magnesium}\,[\text{mg/l}] \times 4.1)$$

(E) Other Components

The biofilm remover of the present invention may contain components other than (A), (B), and (C) as long as the effects of the invention are not impaired. Such other components can be suitably selected according to the intended application and field of application of the biofilm remover. The following are merely examples and are not limiting.

Wound Site Washing Applications

Examples of other components for wound site washing applications include hydrophilic polymers (e.g., caraya gum, pectin, carboxymethylcellulose, hydroxyethylcellulose, and gelatine), hydrophobic polymers (e.g. polyisobutylene (PIB), and styrene isoprene styrene (SIS)), wetting agents (e.g., glycerin and 1,3,-butylene glycol), inorganic salts (e.g., potassium carbonate, calcium carbonate, sodium sesquicarbonate, sodium chloride, potassium chloride, sodium sulfate, magnesium sulfate, sodium metasilicate), and anti-inflammatory components (e.g., dipotassium glycyrrhizate and allantoin).

Oral Cavity Washing Applications

Examples of other components for oral cavity washing applications include wetting agents (e.g., glycerol, propylene glycol, ethanol, and isopropanol), sweeteners (e.g., stevioside, sorbitol, erythritol, and sodium saccharin), disinfectants (e.g., dipotassium glycyrrhizinate, cetylpyridinium chloride, tranexamic acid, isopropyl methylphenol, povidone-iodine, benzalkonium chloride, and chlorhexidine gluconate ethanol), and sodium fluoride.

Topical Skin Applications

Examples include ethanol, glycerol, butylene glycol, dipropylene glycol, propylene glycol, Vaseline, mineral oil, squalane, higher fatty acids, higher alcohols (e.g., stearyl alcohol, behenyl alcohol, and cetanol), fats and oils (e.g., olive oil, coconut oil, shea oil, jojoba seed oil, and horse oil), wax (e.g., beeswax and lanolin), inorganic salts (e.g., potassium carbonate, calcium carbonate, sodium sesquicarbonate, sodium chloride, potassium chloride, sodium sulfate, magnesium sulfate, and sodium metasilicate), herbal medicines and plant extracts (e.g., fennel, *scutellaria* root, *phellodendron* bark, chamomile, *magnolia* bark, *Houttuynia* herb, *calamus, cnidium* rhizome, *Citrus unshiu* peel, Japanese *angelica* root, bitter orange peel, *capsicum, ginseng*, yuzu, wormwood, *saposhnikovia* root and rhizome, *mentha* herb, zinger, *glycyrrhiza*, and cinnamon bark); enzymes (e.g., papain, pancreatin, and proteolytic enzymes), acids (e.g., fumaric acid, succinic acid, malic acid, citric acid, maleic acid, tartaric acid, and lactic acid), moisturizers, vegetable oils (e.g., jojoba oil, olive oil, soya oil, and rice oil), isoflavone, lanolin, glycerol, casein, stearyl alcohol, liquid paraffin, white Vaseline, propylene glycol, skimmed milk powder, squalane, honey, polyethylene glycol, coloring agents, anhydrous silica acid, camphor, methyl salutylate, terpin oil, menthol, dextrin, titanium oxide, and flavoring agents.

Detergent and Disinfectant Applications

Examples include anionic surfactants (e.g., alkyl polyoxyethylene sulfate, linear alkylbenzene sulfonate, and alpha olefin sulfonate), cationic surfactants (e.g., dialkyl dimethyl ammonium chloride and alkyl benzalkonium chloride), amphoteric surfactants (e.g., alkyl betaine, alkyl diethylenetriamino acetic acid, and alkyl amine oxide), non-ionic surfactants (e.g., polyoxyethylene alkyl ether, glycerol fatty acid ester, and polyoxyethylene polyoxypropylene glycol), alkaline compounds (e.g., organic alkali compounds, such as alkanolamine and alkylamine; and hydroxides of alkali metals, such as sodium hydroxide, potassium hydroxide, sodium carbonate, potassium carbonate, sodium hydrogen carbonate, potassium hydrogen carbonate, sodium silicate, potassium silicate, sodium phosphate, and potassium phosphate), solvents (e.g., ethanol, propylene glycol, and glycerol), hydrotrope agents (e.g., paratoluenesulfonic acid, xylene sulfonic acid, and salts thereof), chelating agents (e.g., EDTA, NTA, and MDGA), enzymes (e.g., proteases, amylases, lipases, and cellulases), antioxidants (e.g., butyl hydroxytoluene, sodium sulfite, and sodium hydrogen sulfite), pH-adjusting agents (e.g., citric acid, gluconic acid, malic acid, succinic acid, and acetic acid), thickeners, viscosity modifiers, flavoring agents, coloring agents, and preservatives.

(F) Form, Proportion, Dosage, etc.

The form of the biofilm remover of the present invention includes a composition (one agent) containing components (A), (B), and (C), and a product combination (kit or set) in which at least component (C) is packaged separately from components (A) and (B), and these components are combined when used.

When the biofilm remover of the present invention contains (D) in addition to (A), (B), and (C), the biofilm remover can be a product combination (kit or set) in which at least component (D) is packaged separately from components (A), (B), and (C), and these components are combined when used. Examples include a product combination in which (D) is packaged separately from components (A), (B), and (C), and a product combination in which (D) and (C) are individually packaged separately from (A) and (B).

Further, the biofilm remover of the present invention may be a product combination (kit or set) in which as component (C), a gas generator and its counterpart are packaged separately from each other, and combined when used. In the case of a composition (one agent), the form is not particularly limited as long as it is configured to generate gas for the first time when the composition is added to water. The composition is preferably in the form of a solid. Examples of such solid forms include dry solids, tablets, pills, powders, granules, and capsules.

In the biofilm remover of the present invention, the ratio of components (A), (B), and (C) is not particularly limited as long as the effects of the invention are not impaired.

The ratio can be set, for example, so that the concentrations of components (A), (B), and (C) in a biofilm removal solution prepared by adding water to these components fall within the ranges described below. The water referred to herein (including the case of being simply referred to as "water" in the present specification) includes not only (D) stated above but also various types of water not included in (D), such as other water, aqueous solvents, and aqueous solutions. The water is preferably (D).

When (C) is a $CO_2$ gas generation component, the concentration of component (A) is 0.008 to 0.09 mass %, preferably 0.008 to 0.05 mass %, and more preferably 0.01 to 0.05 mass %;

the concentration of component (B) is 0.0006 to 0.0065 mass %, preferably 0.0006 to 0.004 mass %, and more preferably 0.00075 to 0.004 mass %; and the concentration of component (C) in terms of gas generator is 0.09 to 0.882 mass %, preferably 0.09 to 0.70 mass %, more preferably 0.30 to 0.70 mass %, and particularly preferably 0.40 to 0.70 mass %.

When (C) is a $H_2$ gas generation component, the concentration of component (A) is 0.00009 to 0.1 mass %, preferably 0.0009 to 0.1 mass %, and more preferably 0.0009 to 0.02 mass %;

the concentration of component (B) is 0.00001 to 0.01 mass %, preferably 0.0001 to 0.01 mass %, and more preferably 0.0001 to 0.002 mass %; and the concentration of component (C) in terms of gas generator is 0.001 to 0.9 mass %, preferably 0.001 to 0.1 mass*, and more preferably 0.001 to 0.02 mass %.

When (C) is an $O_2$ gas generation component, the concentration of component (A) is 0.004 to 0.1 mass %, preferably 0.007 to 0.02 mass %, and more preferably 0.008 to 0.02 mass %;

the concentration of component (B) is 0.0005 to 0.02 mass %, preferably 0.0008 to 0.002 mass %, and more preferably 0.0009 to 0.002 mass %; and the concentration of component (C) in terms of gas generator is 0.01 to 0.9 mass %, preferably 0.04 to 0.2 mass %, and more preferably 0.1 to 0.2 mass %.

Action and Effect

When the biofilm remover of the present invention, which contains (A) to (C) above, is added to the target liquid, bubbles are generated in the liquid and the biofilm remover exhibits a biofilm removal effect due to synergy of the surfactant effect of SL and the cleaning effect of bubbles. The bubbles are preferably UFB.

The target liquid may be any liquid in which bubbles, preferably UFB, generate when the biofilm remover of the present invention, which contains (A) to (C) described above, is incorporated into the liquid. The target liquid is not limited but is preferably an aqueous solvent, more preferably an aqueous solvent with a hardness in the range of 30 to 200 mg/L, and particularly preferably an aqueous solvent with a hardness in the range of 50 to 200 mg/L. Water with a hardness in such a range can be suitably used.

Definition and Measurement Method of UFB

Ultrafine bubbles (UFB) are defined as bubbles with a bubble size of less than 1 μm (ISO 20480-1:2017 Fine bubble technology).

UFBs, which are the target of the present invention, are fine bubbles with the bubble size mentioned above. The bubble size of the fine bubbles can be measured using a measuring instrument based on the principle of dynamic light scattering (dynamic light scattering spectrophotometer). Specifically, when the particle size of bubbles contained in a test sample (liquid) is measured, if the average number particle size is less than 1,000 nm, the test sample can be determined to contain UFBs. The average number particle size of UFBs may be less than 1,000 nm, and the lower limit is not particularly limited. UFBs can be classified into fine bubbles with an average number particle size of 50 nm to less than 200 nm, fine bubbles with an average number particle size of 200 nm to less than 500 nm, and fine bubbles with an average number particle size of 500 nm to less than 1,000 nm. UFBs are preferably fine bubbles with an average number particle size of 500 nm or less. Below, the terms "particle size" and "bubble size" in the present specification indicate the average number particle size.

In order for a liquid containing fine bubbles (UFBs) having a bubble size of less than 1,000 nm to effectively exhibit its function, it is preferable that the liquid contains the UFBs in the predetermined concentration ratio. UFBs in the liquid make a particle size-dependent Brownian motion. Accordingly, by irradiating a UFB-containing liquid with laser light (He—Ne mode) and detecting emitted scattered light with a dynamic light scattering spectrophotometer, the scattering intensity, which depends on the Brownian motion of the UFB particles, can be measured. Therefore, the ratio (concentration) of UFBs in the liquid can be evaluated by measuring the scattering intensity (cps) of the UFBs in the UFB-containing liquid. The specific measurement method and conditions are as described in Experimental Example 1. As described below, the scattering intensity of the UFBs in the UFB-containing liquid can be evaluated by subtracting the scattering intensity due to particles other than UFBs from the scattering intensity of the UFB-containing liquid. The scattering intensity of UFBs is not limited, and is preferably 5,000 cps or more, more preferably 10,000 cps or more, and particularly preferably 30,000 cps or more. The scattering intensity of UFBs is not particularly limited as long as the upper limit of the scattering intensity of UFBs is 100,000,000 cps.

From the scattered light obtained by the above method, the autocorrelation function using the photon correlation method is obtained. The diffusion coefficient, which indicates the Brownian motion velocity, as well as the particle size and particle size distribution, can be obtained by using cumulant analysis and histogrammatic analysis. In the present invention, the UFB particle size can be measured and evaluated according to the method and conditions shown in Experimental Example 1 below.

Unlike millibubbles, which quickly rise to the surface of a liquid and burst, and microbubbles, which float gently and disappear, UFBs, once formed in a liquid, are known to float and be retained for a long period of time while diffusing in the liquid through Brownian motion without rising. In the present invention as well, it is also desirable that the scattering intensity continues over a long period of time. The period of continuation of the scattering intensity is not limited, and can last, for example, on a daily basis, such as for one day to several days; on a monthly basis, such as for one month to several months; or a yearly basis, such as for one year to several years.

Specifically, the particle size of UFBs and the scattering intensity can be determined by using a dynamic light scattering spectrophotometer (DLS 6500-HL: produced by Otsuka Electronics Co., Ltd) at atmospheric pressure and room temperature (25° C.) under the following conditions.

Laser mode: He—Ne laser
Number of integrations: 400 times
Sampling time: 10 μsec
Measurement channel: 1024 ch
Measuring angle: 30°
Pinhole 1: 0.5
Pinhole 2: 0.2

(II) Method for Using the Biofilm Remover

The biofilm remover of the present invention is used to prepare a biofilm removal solution by adding the biofilm remover to water with a hardness of 30 to 200 mg/L, and preferably 50 to 200 mg/L, and allowing these three components (A), (B), and (C) to all be present in water at the concentrations within the ranges described below. By preparing the biofilm removal solution in this manner, UFBs can be generated in the biofilm removal solution without particularly introducing gas from the outside.

When (C) is a $CO_2$ gas generation component, the concentration of component (A) is 0.008 to 0.09 mass %, preferably 0.008 to 0.05 mass %, and more preferably 0.01 to 0.05 mass %, the concentration of component (B) is 0.0006 to 0.0065 mass %, preferably 0.0006 to 0.004 mass %, and more preferably 0.00075 to 0.004 mass %, and the concentration of component (C) in terms of gas generator is 0.09 to 0.882 mass %, preferably 0.09 to 0.70 mass %, more preferably 0.30 to 0.70 mass %, and particularly preferably 0.40 to 0.70 mass %.

When (C) is a $H_2$ gas generation component, the concentration of component (A) is 0.00009 to 0.1 mass %, preferably 0.0009 to 0.1 mass %, and more preferably 0.0009 to 0.02 mass %, the concentration of component (B) is 0.00001 to 0.01 mass %, preferably 0.0001 to 0.01 mass %, and more preferably 0.0001 to 0.002 mass %, and the concentration of component (C) in terms of gas generator is 0.001 to 0.9 mass %, preferably 0.001 to 0.1 mass %, and more preferably 0.001 to 0.02 mass %.

When (C) is an $O_2$ gas generation component, the concentration of component (A) is 0.004 to 0.1 mass %, preferably 0.007 to 0.02 mass %, and more preferably 0.008 to 0.02 mass %, the concentration of component (B) is 0.0005 to 0.02 mass %, preferably 0.0008 to 0.002 mass %, and more preferably 0.0009 to 0.002 mass %, and the concentration of component (C) in terms of gas generator is 0.01 to 0.9 mass %, preferably 0.04 to 0.2 mass %, and more preferably 0.1 to 0.2 mass %.

The temperature of the water to which the biofilm remover is added is not particularly limited as long as it is a temperature at which the generation of UFBs is not impaired. The temperature of the water is preferably 50° C. or less. A biofilm remover in which components (A), (B), and (C) are in a previously mixed state (in the form of a single composition) can also be used. In this case, the composition can be added to water as is. Further, a biofilm remover (set or kit) in which at least component (C) is packaged separately from components (A) and (B) can also be used. In this case, it is also possible to mix the three components (A) to (C) before adding to water when used, or simultaneously add these three components to water when used. It is also possible to use, as water, (D) that is packaged separately from components (A) to (C) in the biofilm remover (product combination).

The water with a hardness of 30 to 200 mg/L includes tap water, distilled water, ion-exchanged water, and sterile water as well as aqueous solutions containing various components, depending on the intended application or field of application (such as the medical and pharmaceutical field, the cosmetic field, and the food and beverage field). Examples of such components include, without limitation, component (E) as described above.

In one example, in the case of preparing a detergent for use to remove a biofilm from a mammal, including humans, as a subject, when the biofilm remover of the present invention is incorporated into water with a hardness of 30 to 200 mg/L so that the concentrations of components (A), (B), and (C) fall within the ranges described above, the desired bubbles, preferably UFB, can be generated in the water. Since the biofilm removal solution with bubbles, preferably UFB, has low cytotoxicity in addition to biofilm removal effects, the biofilm removal solution can be formed and obtained as a detergent that is less invasive and is safe for the human body. The biofilm removal solution with the bubbles may be prepared at the time of each use, or it may be prepared at the time of first use and continued to be used within the range in which the effect is exhibited because UFBs among bubbles are stably retained in water.

The biofilm removal solution with bubbles (preferably UFB) thus prepared is used by bringing the biofilm removal solution into contact with the target site of a mammal having a biofilm formed or having a potential of having a biofilm formed. The phrase "having a potential of having a biofilm formed" includes having the probability that bacteria that cause biofilm formation may form a biofilm. In other words, the biofilm removal solution can be preferably used to prevent biofilm formation by removing bacteria that cause biofilm formation (i.e., the biofilm formation prevention), as well as to remove a biofilm. In this way, the biofilm removal solution of the present invention can also be used to fundamentally remove a biofilm.

Although this is not limitative, the biofilm removal can be effectively performed by applying the biofilm removal solution containing bubbles (preferably UFB) to the target site of a mammal during the period from the attachment of bacteria that cause biofilm formation to the formation of a mature biofilm. Although this is not limitative, the biofilm removal solution containing bubbles (preferably UFB) is preferably applied within 24 hours from the attachment of the bacteria that cause biofilm formation.

The presence of a biofilm in a target site of a mammal can be detected by a known method. For example, the presence of the biofilm on the wound surface of a human can be detected by using the wound surface blotting method or the biofilm detection reagent kit described above in the Background Art section (NPL 2 to NPL 5 and PTL 1). In particular, a biofilm detection reagent kit is commercially available as a Biofilm Detection Tool (a biofilm detection solution and a membrane sheet for sample collection) (produced by Saraya Co., Ltd.) and can be easily used.

The target site of a mammal includes a wound site, a peri-wound site, skin other than the wound site and the peri-wound site, and the oral cavity of a mammal. The target site is preferably a wound site or a peri-wound having a high risk of infection due to biofilm formation. The mammal includes humans.

The method for bringing the biofilm removal solution into contact with a mammal may be any method that can remove a biofilm by bringing the biofilm removal solution into contact with the target site of a mammal. Examples of the method include, but are not limited to, spraying, application, immersion, washing, and the like, and are not particularly limited.

Biofilm Removal Method

The method for removing a biofilm by using the biofilm removal solution is not limited but can be specifically carried out, for example, in the following manner.

Specifically, when the target site to be washed is a wound site, peri-wound site, skin, or dental surface, the biofilm removal solution is placed in a container capable of spraying or ejecting the content and is sprayed or ejected onto the target site so as to bring the biofilm removal solution into contact with the target site. When the biofilm removal solution is sprayed or ejected onto the target site, the target site can be rubbed by using a soft manual or electric washing brush that does not damage the target site, if necessary. The container into which the biofilm removal solution is placed may be any container that has the mechanism of allowing the biofilm removal solution in the container to be sprayed or ejected outwards, and is not particularly limited. Specific examples include wound site cleaning kits, cleaning device kits, electric biological cleaning devices, aseptic manual biological cleaning devices, manual biological cleaning devices of medical device class III, wash bottles, push bottles capable of discharging liquid like a shower, injection syringe-like devices capable of ejecting liquid by pushing, manual spray bottles, electric spray bottles, bottles capable of pumping out liquid, containers capable of discharging liquid like a shower, such as water jars, droppers, and electric pulse cleaning vessels. After the target site is washed with the biofilm removal solution, the target site can be rinsed with saline, distilled water, or tap water, if necessary.

When the target site from which a biofilm is removed is the oral cavity, the biofilm removal solution is held in the oral cavity and the mouth is rinsed while making sounds in the mouth. The biofilm removal solution is held in the mouth for 15 to 60 seconds, and preferably 20 to 30 seconds. During that time, the oral cavity can be rubbed with a soft manual or electric washing brush that does not damage the oral cavity. The mouth is then rinsed with saline, tap water, or the like.

The biofilm removal solution used here can be prepared by the method for preparing the biofilm removal solution described above, although the method is not limited thereto. For example, when the biofilm removal solution is prepared by using a powdery biofilm remover containing at least components (A) and (B), the biofilm remover is added to water in a container having a function to discharge the content in such an amount that components (A) and (B) each have a specific concentration and are dissolved in the water, if necessary, with shaking. It is also possible to prepare a covering material for biofilm removal by impregnating a covering material, such as gauze and film, with the prepared biofilm removal solution. In this case, when the biofilm removal solution is prepared by using a polymer having low toxicity in addition to water, evaporation of the biofilm removal solution from the covering material can be suppressed. Covering the target site (e.g., a wound site, a peri-wound site) with the covering material for biofilm removal thus prepared can allow the biofilm removal solution to remain at the target site for a longer period of time. The time for applying the covering material for biofilm removal is 10 minutes to 48 hours, and preferably 10 minutes to 24 hours. After removing the covering material, the target site may be rinsed with saline, distilled water, tap water, or the like, if necessary.

The concentrations of components (A), (B), and (C) in the biofilm removal solution prepared by the above method are as described in (I). Including the description about the amounts of the components used when mixed with water (concentrations in water), the hardness of the water used, the scattering intensity of UFB generated, and the particle size, the descriptions in (I) can also be applied here.

(III) Biofilm Removal Solution and Production Method thereof

The biofilm removal solution of the present invention is characterized by comprising the following (A), (B), (c), and (d):

(A) an SL containing acidic SL and lactonic SL in a ratio of 78:22 to 100:0 (a mass ratio);

(B) a free fatty acid or a salt thereof;

(c) fine bubbles that are formed from at least one gas selected from the group consisting of $CO_2$ gas, $H_2$ gas, $O_2$ gas, and that have an average number particle size of less than 1,000 nm; and (d) water.

The types and amounts (concentrations) of component (A), component (B), and the gas generator, which is a raw material for producing component (c), are as explained in (I). Such descriptions in (I) are incorporated herein by reference. Component (d) is preferably water with a hardness of 30 to 200 mg/L, and more preferably 50 to 200 mg/L. Water in which component (E) is dissolved can also be used as long as the water does not deviate from the range of hardness of 30 to 200 mg/L. The component (E) can be appropriately selected and used according to the intended application and field of application (such as the medical and pharmaceutical field, the cosmetic field, and the food and beverage field). The biofilm removal solution of the present invention can be used in various fields mentioned above according to component (E).

As described above in (II), the biofilm removal solution of the present invention is preferably used for the target site of a mammal that has a biofilm formed or that has a potential of having a biofilm formed (e.g., a wound site, a peri-wound site, skin other than the wound site and the peri-wound site, and the oral cavity). The target site is preferably a wound site or a peri-wound site where the risk of infection is high due to biofilm formation.

The USBs in the biofilm removal solution of the present invention may have a particle size of less than 1,000 nm. The USBs contain fine bubbles with a particle size of 50 nm to less than 200 nm, fine bubbles with a particle size of 200 nm to less than 500 nm, and fine bubbles with a particle size of 500 nm to less than 1,000 nm. The USBs are preferably fine bubbles with a particle size of 500 nm or less.

When the biofilm removal solution of the present invention is used, the scattering intensity as measured by the method described above is preferably 5,000 cps or more, more preferably 10,000 cps or more, and particularly preferably 30,000 cps or more, although this is not limitative.

The biofilm removal solution of the present invention can be produced by the following method. The method for producing a biofilm removal solution comprises the steps of:

(a) adding (A), (B), and (C) described below to water with a hardness of 30 to 200 mg/L, preferably a hardness of 50 to 200 mg/L, to allow these three components to all be present in the water; and (b) generating bubbles in the water, wherein (A) is an SL containing acidic SL and lactonic SL in a ratio of 78:22 to 100:0 (mass ratio), (B) is a free fatty acid or a salt thereof, and (C) is a gas generation component.

According to this method, without particularly introducing gas from the outside, UFBs can be generated in water and a UFB-containing biofilm removal solution can be prepared and obtained. According to the biofilm removal solution thus prepared, bringing the biofilm removal solution into contact with the target site of a mammal having a biofilm formed or a mammal having a potential of having a biofilm formed (e.g., a wound site or a peri-wound site, skin other than the wound site and the peri-wound site, and the oral cavity of a mammal) can remove the biofilm. Further, biofilm formation can be prevented (biofilm formation prevention) by removing bacteria that cause biofilm formation (biofilm formation prevention) as well as removing a biofilm.

The terms "comprising" and "containing" in the present specification include the meaning of consisting of and consisting essentially of.

EXAMPLES

In order to aid understanding of the structure and effect of the present invention, the present invention is described below with reference to experimental examples. However, the present invention is not limited to these experimental examples. Unless otherwise specified, the following experiments were conducted at room temperature (25±5° C.) under atmospheric pressure. Unless otherwise specified, "%" stated below means mass %, and "parts" stated below means parts by mass.

Reference Production Example 1: Preparation of SL-Containing Composition (1) A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of yeast extract (produced by Asahi Food & Healthcare Co., Ltd., product name: Meast Powder N) was used as a culture medium. *Candida bombicola* ATCC22214 was cultured in the liquid medium while being shaken at 30° C. for 2 days. This was used as a pre-culture liquid.

(2) The pre-culture liquid was inoculated in a proportion of 4% into a main culture medium (3 L) placed in a 5-liter fermenter, and then cultured at 30° C. at an aeration rate of 0.6 vvm for 6 days for fermentation. The main culture medium contained, per liter, 100 g of aqueous glucose, 50 g of palm olean (produced by NOF Corporation, product name: Palmary 2000), 50 g of oleic acid (produced by Acid Chem, product name: Palmac 760), 1 g of sodium chloride, 10 g of monopotassium phosphate, 10 g of magnesium sulfate heptahydrate, 2.5 g of yeast extract (produced by Asahi Food & Healthcare Co., Ltd., product name: Meast Powder N), and 1 g of urea (pH of 4.5 to 4.8 before sterilization).

On the sixth day from the start of culture, the fermentation was ended. The liquid culture removed from the fermenter was heated and then returned to room temperature and allowed to stand for 2 to 3 days. As a result, the liquid culture was separated into the following three layers in this order from the bottom: a liquid brown precipitate layer, a milky-white solid layer presumably mainly containing fungal cells, and a supernatant. After the supernatant was removed, industrial water or groundwater was added in an amount equal to the amount of the supernatant removed. While the resulting mixture was stirred, a 48 mass % aqueous sodium hydroxide solution was gradually added to adjust the pH to 6.5 to 6.9, thus solubilizing SLs contained in the liquid culture. The resulting product was centrifuged with a table-top centrifuge (Westfalia, produced by Westfalia Separator AG) to precipitate milky-white solids, and a supernatant was collected. While the collected supernatant was stirred, 62.5 mass % of sulfuric acid was gradually added to adjust the pH to 2.5 to 3.0, thus insolubilizing SLs again. After the resulting mixture was allowed to stand for 2 days, the supernatant was removed as much as possible by decantation. The residue was obtained as an SL-containing composition (having a water content of about 50).

Reference Production Example 2: Preparation of SL-Containing Composition 1

An aqueous sodium hydroxide solution was added to the SL-containing composition obtained in Reference Production Example 1 to adjust the pH to 14, and the mixture was treated at 80° C. for 2 hours for hydrolysis (alkali hydrolysis). Then, the resultant was returned to room temperature, and the pH was adjusted to 10 with sulfuric acid (9.8 M aqueous solution). The insoluble matter produced was removed by filtration, and the filtrate was obtained as SL-containing composition 1 (having a water content of about 30%). SL-containing composition 1 contained SL (acidic SL:lactonic SL=100:0 (mass ratio)) in an amount of 34% and oleic acid in an amount of 2.5%.

Reference Production Example 3: Preparation of SL-Containing Composition 2

SL-containing composition 1 prepared in Reference Production Example 2 was purified according to Example 1 of WO2015/034007A, and powder was obtained as SL-containing composition 2. SL-containing composition 2 contained SL in an amount of 99.8% (acidic SL:lactonic SL=100:0 (mass ratio)) and oleic acid in an amount of 0.2%.

Preparation Example 1: Preparation of Biofilm Remover and Biofilm Removal Solution ($CO_2$ Gas Generation)

Biofilm removers (for $CO_2$ gas generation) were prepared by combining SL-containing composition 1 and sodium hydrogen carbonate (formulas 1 and 2) or by combining SL-containing composition 2, sodium hydrogen carbonate, and fatty acid (formula 3) in the proportions listed in Table 1. Then, the biofilm removers were individually added to tap water (hardness 100 mg/L; room temperature) in a glass beaker such that the concentration of the resulting biofilm removal solutions (the content of formulated product in an aqueous solution) ranged from 0.1 to 0.9%, and stirred and dissolved using a stirring bar and an agitator, thereby preparing biofilm removal solutions (Test Samples 1-1 to 1-4, Test Samples 2-1 to 2-6, and Test Sample 3-1) (a pH of 8.0 to 8.5). Table 2 shows the percentage (%) of each component in the biofilm removal solutions. The biofilm removal solutions all produced $CO_2$ gas when all components were dissolved in water.

TABLE 1

Formulas of Biofilm Remover (for $CO_2$ Gas Generation)

Mass %

| | | Test Sample | | | | | | | | | | |
|---|---|---|---|---|---|---|---|---|---|---|---|---|
| | | Formula 1 | | | | Formula 2 | | | | | | Formula 3 |
| | | 1-1 | 1-2 | 1-3 | 1-4 | 2-1 | 2-2 | 2-3 | 2-4 | 2-5 | 2-6 | 3-1 |
| A and B | SL-containing Composition 1 | 6 | | | | 30 | | | | | | 0 |
| | (A: Acidic SL) | (2.04) | | | | (10.2) | | | | | | |
| | (B: Free Fatty Acid) | (0.15) | | | | (0.75) | | | | | | |
| A and B | SL-containing Composition 2 | 0 | | | | 0 | | | | | | 2 |
| | (A: Acidic SL) | | | | | | | | | | | (1.996) |
| | (B: Free Fatty Acid) | | | | | | | | | | | (0.004) |
| B | Oleic Acid | 0 | | | | 0 | | | | | | 0.2 |
| C | Sodium Hydrogen Carbonate | 97.81 * | | | | 89.05 * | | | | | | 97.8 |
| Total Free Fatty Acid Concentration in Formulation/% | | 0.15 | | | | 0.75 | | | | | | 0.2004 |
| Concentration of Biofilm Removal Solution/% | | 0.4 | 0.5 | 0.7 | 0.9 | 0.1 | 0.2 | 0.25 | 0.4 | 0.5 | 0.88 | 0.5 |

* The percentage (mass %) out of the total of A (acidic SL), B (free fatty acid), and C (sodium hydrogen carbonate) taken as 100 mass % (on a dry weight basis)

TABLE 2

Biofilm Removal Solution and Evaluation Results

Mass %

| | | Test Sample | | | | | |
|---|---|---|---|---|---|---|---|
| | | Formula 1 | | | | Formula 2 | |
| | | 1-1 | 1-2 | 1-3 | 1-4 | 2-1 | 2-2 |
| A and B | SL-containing Composition 1 | 0.024 | 0.03 | 0.042 | 0.054 | 0.03 | 0.06 |
| | (A: Acidic SL) | (0.008) | (0.01) | (0.014) | (0.018) | (0.01) | (0.02) |
| | (B: Free Fatty Acid) | (0.0006) | (0.00075) | (0.001) | (0.0014) | (0.00075) | (0.0015) |
| A and B | SL-containing Composition 2 | 0 | 0 | 0 | 0 | 0 | 0 |
| | (A: Acidic SL) | | | | | | |
| | (B: Free Fatty Acid) | | | | | | |
| B | Oleic Acid | 0 | 0 | 0 | 0 | 0 | 0 |
| C | Sodium Hydrogen Carbonate | 0.392 | 0.49 | 0.686 | 0.882 | 0.09 | 0.18 |
| Water (Hardness: 100 mg/L) | | Remainder | Remainder | Remainder | Remainder | Remainder | Remainder |
| Total Amount | | 100 | 100 | 100 | 100 | 100 | 100 |
| Total Free Fatty Acid Concentration in Water/% | | 0.0006 | 0.00075 | 0.001 | 0.0014 | 0.00075 | 0.0015 |
| Generated Gas | | $CO_2$ | $CO_2$ | $CO_2$ | $CO_2$ | $CO_2$ | $CO_2$ |
| Evaluation | Scattering Intensity | — | AA | — | — | AA | — |
| of UFB | Average Number Particle Size | — | AA | — | — | AA | — |
| Evaluation Result of Removal Effect | | A | A | AA | AA | A | A |
| Cell Viability/% (L929 cell 48 h) | | >100 | >100 | 78.8 | 53.4 | 90.5 | 92.3 |
| (Evaluation Result) | | (AA) | (AA) | (AA) | (A) | (AA) | (AA) |
| Cell Viability/% (V79 cell 48 h) | | >100 | >100 | 85.8 | 55.5 | 97.5 | 97.3 |
| (Evaluation Result) | | (AA) | (AA) | (AA) | (A) | (AA) | (AA) |

Mass %

| | | Test Sample | | | | |
|---|---|---|---|---|---|---|
| | | Formula 2 | | | | Formula 3 |
| | | 2-3 | 2-4 | 2-5 | 2-6 | 3-1 |
| A and B | SL-containing Composition 1 | 0.075 | 0.12 | 0.15 | 0.26 | 0 |
| | (A: Acidic SL) | 0.025) | (0.04) | (0.05) | (0.088) | |
| | (B: Free Fatty Acid) | (0.0019) | (0.003) | (0.004) | (0.0065) | |
| A and B | SL-containing Composition 2 | 0 | 0 | 0 | 0 | 0.01 |
| | (A: Acidic SL) | | | | | (0.00998) |
| | (B: Free Fatty Acid) | | | | | (0.00002) |
| B | Oleic Acid | 0 | 0 | 0 | 0 | 0.001 |
| C | Sodium Hydrogen Carbonate | 0.225 | 0.36 | 0.45 | 0.792 | 0.49 |
| Water (Hardness: 100 mg/L) | | Remainder | Remainder | Remainder | Remainder | Remainder |
| Total Amount | | 100 | 100 | 100 | 100 | 100 |
| Total Free Fatty Acid Concentration in Water/% | | 0.0019 | 0.003 | 0.004 | 0.0065 | 0.00102 |

TABLE 2-continued

Biofilm Removal Solution and Evaluation Results

| | | | | | | |
|---|---|---|---|---|---|---|
| Generated Gas | | $CO_2$ | $CO_2$ | $CO_2$ | $CO_2$ | $CO_2$ |
| Evaluation of UFB | Scattering Intensity | AA | — | AA | — | AA |
| | Average Number Particle Size | AA | — | AA | — | AA |
| Evaluation Result of Removal Effect | | A | A | AA | AA | A |
| Cell Viability/% (L929 cell 48 h) | | 92.8 | 94.0 | 94.5 | 61.5 | >100 |
| (Evaluation Result) | | (AA) | (AA) | (AA) | (A) | (AA) |
| Cell Viability/% (V79 cell 48 h) | | 97.2 | 92.5 | 89.5 | 60.4 | >100 |
| (Evaluation Result) | | (AA) | (AA) | (AA) | (A) | (AA) |

—: Not Measured

Experimental Example 1: Evaluation of Ultrafine Bubble Generation

(1) Experimental Procedure

The biofilm removal solutions (Test Sample 1-2, Test Samples 2-1, 2-3, and 2-5, and Test Sample 3-1) prepared in the Preparation Example were allowed to stand at room temperature for 12 hours, and then the scattering intensity and average number particle size (simply "particle size" below) were measured. For the measurements of scattering intensity and particle size, a dynamic light scattering spectrophotometer (DLS 6500-HL: produced by Otsuka Electronics Co., Ltd.) was used. Specifically, the biofilm removal solutions prepared in the Preparation Example were each filtered (with a filter with a pore size of 0.45 μm) using a 10-mL syringe to remove solid impurities, and the filtrate was collected in a cylindrical measurement cell with a diameter of 21 mm. The collected filtrate was used in the dynamic light scattering spectrophotometer as a measurement sample under the following conditions.

Measurement Conditions for Dynamic Light Scattering Spectrophotometer

Measurement temperature: 25° C.

Cumulated number: 400 times

Sampling time: 10 μsec

Measurement channel: 1024 ch

Measurement angle: 30°

Pinhole 1: 0.5

Pinhole 2: 0.2

As shown in Equation 1 below, the scattering intensity was calculated by subtracting the scattering intensity of an aqueous solution of components A and B used in each Test Sample (SL-containing composition 1 (Formula 1), SL-containing composition 2 (Formula 2), or SL-containing composition 2 and fatty acid (Formula 3)) (Control Sample 1) and the scattering intensity of an aqueous solution of component C (sodium hydrogen carbonate) used in each Test Sample (Control Sample 2). Tap water (hardness: 100 mg/L) with a scattering intensity of 585 cps was used to dissolve each component.

Scattering intensity=(scattering intensity of Test Sample)−(scattering intensity of Control Sample 1)−(scattering intensity of Control Sample 2) Equation 1

Evaluation was performed from the obtained scattering intensity and particle size on the basis of the following criteria.

Scattering Intensity

AA: 30,000 cps or more

A: 10,000 cps or more and less than 30,000 cps

B: 5,000 cps or more and less than 10,000 cps

C: less than 5,000 cps

Average Number Particle Size

AA: 50 nm or more and less than 200 nm

A: 200 nm or more and less than 500 nm

B: 500 nm or more and less than 1,000 nm

C: 1,000 nm or more

(2) Experimental Results

Table 2 above shows the results. As shown in Table 2, adding acidic SL, a free fatty acid, and a gas generation component (hydrogen carbonate) in combination to water was confirmed to generate $CO_2$ bubbles and enable the $CO_2$ bubbles to remain stable and present in water after being left for at least 12 hours. From their particle size and scattering intensity, the bubbles were also confirmed to be fine bubbles equivalent to ultrafine bubbles (UFB). Using a biofilm removal solution prepared with water with a hardness of 30 mg/L instead of using water with a hardness of 100 mg/L also generates fine bubbles equivalent to ultrafine bubbles (UFB) in the same manner.

Experimental Example 2: Evaluation of Biofilm Removal Effect

(1) Experimental Procedure

The biofilm removal effect of the biofilm removal solutions (Test Samples 1-1 to 1-4, Test Samples 2-1 to 2-6, and Test Sample 3-1) prepared in the Preparation Example was evaluated by using a biofilm model prepared in a 24-well plate according to the following method.

Preparation of Biofilm Model

Streaking of *P. aeruginosa* (PAO-1) (test bacteria) was performed in a TSA medium, and the bacteria were incubated at 37° C. for 72 hours.

After incubation, the test bacteria were suspended in physiological saline to prepare a bacterial solution of about $10^8$ to $10^9$ CFU/mL. This test solution of bacteria was diluted stepwise with physiological saline to $10^2$ to $10^3$ CFU/mL.

The test solution of bacteria in an amount of 1% was mixed with a Y medium in a centrifuge tube to result in $10^3$ CFU/mL and inoculated in an amount of 2 mL/well into a 24-well plate (Corning Incorporated, polystyrene, surface treated for cell culture).

The test solution of bacteria in the 24-well plate was incubated at 37° C. for 18 hours.

After incubation, the medium was removed, and the remainder was used as a biofilm model.

The formation of a biofilm in this biofilm model was confirmed beforehand by staining with a 0.1% crystal violet solution.

Evaluation Test of Biofilm Removal Effect

The biofilm removal solutions (Test Samples 1-1 to 1-4, Test Samples 2-1 to 2-6, and Test Sample 3-1) were individually added to each well in an amount of 500 μL with a micropipette and allowed to act for 3 minutes, during which a physical force was applied with a bench-top shaker (wave-SI: Taitec Corporation, shaking motion: seesaw shaking, angle: 2 to 10°) at a speed of 50 r/min for 3 minutes.

The biofilm removal solutions were removed, and the wells were washed with physiological saline.

500 μL of a 0.1% crystal violet solution was added to each well and allowed to stand for 15 minutes to stain the biofilm.

After 15 minutes, the crystal violet solution was removed, and the wells were washed with physiological saline.

The degree of staining of the 24-well plate was visually observed and evaluated based on the following criteria.

Criteria for Evaluation of Removal Effect

AA: 50% or higher of the biofilm was removed.

A: 30% or higher and less than 50% of the biofilm was removed.

B: 15% or higher and less than 30% of the biofilm was removed.

C: More than 85% staining remained (little or no biofilm removal effect was observed).

A biofilm model that did not undergo removal with a biofilm removal solution and washing with physiological saline (unwashed) was stained with a crystal violet solution according to the method described above, and the degree of staining (visual evaluation) of the biofilm model was taken as 100%. Without inoculation of the bacteria, a 24-well plate itself was stained with a crystal violet solution, and the degree of staining (visual evaluation) was taken as 0%.

(2) Experimental Results

Table 2 shows the results. As shown in Table 2, all of the biofilm removal solutions were confirmed to have an effect in removing 30% or higher of the biofilm. In particular, Test Samples 1-3, 1-4, 2-5, and 2-6 showed a high degree of a biofilm removal effect. The biofilm removal effect was significantly reduced when the SL content in the biofilm removal solution was 0.005 mass % or lower.

Experimental Example 3: Safety Evaluation (1) Experimental Procedure

The safety of the biofilm removal solutions prepared in the Preparation Example (Test Samples 1-1 to 1-4, Test Samples 2-1 to 2-6, and Test Sample 3-1) was evaluated by using two types of cells with different sensitivities. The biofilm removal solutions were prepared by dissolving a biofilm remover in a medium specified by the ISO, indicated below (Eagle MEM medium: 200 mg/L hardness), instead of the water described above, and were subjected to filter sterilization beforehand. Use of the medium with a hardness of 200 mg/L instead of water with a hardness of 100 mg/L also gave results similar to those shown in Table 2 ($CO_2$ gas generation, UFB formation, and biofilm removal effect).

Target Cell

L929 cells (NCTC clone 929, fibroblasts in mouse subcutaneous tissue)

V79 cells (JCRB 0603, Chinese hamster lung-derived fibroblasts)

With reference to ISO-10993-5:-2009 (annex C, MTT cytotoxicity test), the experiment was conducted accordingly (the duration of action being changed to 48 hours), and evaluation was performed based on the following criteria.

Safety Evaluation Criteria

AA: Cell viability: 70% or higher

A: Cell viability: 50% or higher

C: Cell viability: less than 50%

The same test using physiological saline (0.85% aqueous sodium chloride solution) instead of the biofilm removal solutions showed a cell viability of 76.5% in L929 cells and 2.4% in V79 cells.

(2) Experimental Results

Table 2 above shows the results. As shown in Table 2, both types of cells were confirmed to have had a high cell viability of 50% or higher with any of the biofilm removal solutions. In particular, the cell viability with Test Samples 1-1 to 1-3, 2-1 to 2-5, and 3-1 was higher than that with physiological saline, indicating that the test samples were highly safe for living organisms. A content of sodium hydrogen carbonate of 0.9 mass % or higher in the biofilm removal solutions tended to increase cytotoxicity.

Experimental Example 4: Comparative Experiment

In accordance with the comparative formulas 1 to 3 listed in Tables 3 and 4, the components were added to 1 L of tap water (hardness: 100 mg/L, room temperature) in a glass beaker, and stirred and dissolved using a stirring bar and an agitator, thereby preparing Comparative Test Samples 1-1 to 1-6, Comparative Test Samples 2-1 to 2-3 (Table 3), and Comparative Test Samples 3-1 to 3-9 (Table 4).

TABLE 3

Formulas of Comparative Test Samples and Evaluation Results

Mass %

| | | Test Sample | | | | | | | | |
|---|---|---|---|---|---|---|---|---|---|---|
| | | Comparative Formula 1 | | | | | | Comparative Formula 2 | | |
| | | 1-1 | 1-2 | 1-3 | 1-4 | 1-5 | 1-6 | 2-1 | 2-2 | 2-3 |
| A and B | SL-containing Composition 2 (A: Acidic SL) (B: Free Fatty Acid) | 0 | 0 | 0 | 0 | 0 | 0 | 0 | 0 | 0 |
| B | Oleic Acid | 0 | 0 | 0 | 0 | 0 | 0 | 0.0006 | 0.00075 | 0.001 |
| C | Sodium Hydrogen Carbonate | 0.392 | 0.4 | 0.5 | 0.88 | 0.9 | 1 | 0 | 0 | 0 |
| Water (Hardness: 100 mg/L) | | Remainder | Remainder | Remainder | Remainder | Remainder | Remainder | Remainder | Remainder | Remainder |
| Total Amount | | 100 | 100 | 100 | 100 | 100 | 100 | 100 | 100 | 100 |

TABLE 3-continued

Formulas of Comparative Test Samples and Evaluation Results

Mass %

| | | Test Sample: Comparative Formula 1 | | | | | | Comparative Formula 2 | | |
|---|---|---|---|---|---|---|---|---|---|---|
| | | 1-1 | 1-2 | 1-3 | 1-4 | 1-5 | 1-6 | 2-1 | 2-2 | 2-3 |
| Total Free Fatty Acid Concentration in Water/% | | 0 | 0 | 0 | 0 | 0 | 0 | 0.0006 | 0.00075 | 0.001 |
| Generated Gas | | $CO_2$ | $CO_2$ | $CO_2$ | $CO_2$ | $CO_2$ | $CO_2$ | None | None | None |
| Evaluation of UFB | Scattering Intensity | C | C | C | C | C | C | C | C | C |
| | Average Number Particle Size | C | C | C | C | C | C | C | C | C |
| Evaluation Result of Removal Effect | | C | C | C | C | C | C | C | C | A |
| Cell Viability/% (L929 cell 48 h) (Evaluation Result) | | 91.4 (AA) | 91.1 (AA) | 88.1 (AA) | 50.4 (A) | 48.0 (C) | 36.8 (C) | — | — | — |
| Cell Viability/% (V79 cell 48 h) (Evaluation Result) | | 94.2 (AA) | 94.3 (AA) | 95.5 (AA) | 49.7 (C) | 47.4 (C) | 36.7 (C) | — | — | — |

—: Not Measured

TABLE 4

Formulas of Comparative Test Samples and Evaluation Results

Mass %

| | | Test Sample Comparative Formula 3 | | | | |
|---|---|---|---|---|---|---|
| | | 3-1 | 3-2 | 3-3 | 3-4 | 3-5 |
| A and B | SL-containing Composition 2 | 0.005 | 0.008 | 0.01 | 0.014 | 0.018 |
| | (A: Acidic SL) | (0.00499) | (0.007984) | (0.00998) | (0.01397) | (0.0180) |
| | (B: Free Fatty Acid) | (0.00001) | (0.000016) | (0.00002) | (0.000028) | (0.000036) |
| B | Oleic Acid | 0 | 0 | 0 | 0 | 0 |
| C | Sodium Hydrogen Carbonate | 0 | 0 | 0 | 0 | 0 |
| Water (Hardness: 100 mg/L) | | Remainder | Remainder | Remainder | Remainder | Remainder |
| Total Amount | | 100 | 100 | 100 | 100 | 100 |
| Total Free Fatty Acid Concentration in Water/% | | 0.00001 | 0.000016 | 0.00002 | 0.000028 | 0.000036 |
| Generated Gas | | None | None | None | None | None |
| Evaluation of UFB | Scattering Intensity | C | C | C | C | C |
| | Average Number Particle Size | C | C | C | C | C |
| Evaluation Result of Removal Effect | | C | C | C | C | C |
| Cell Viability/% (L929 cell 48 h) (Evaluation Result) | | — | — | — | — | — |
| Cell Viability/% (V79 cell 48 h) (Evaluation Result) | | — | — | — | — | — |

Mass %

| | | Test Sample Comparative Formula 3 | | | |
|---|---|---|---|---|---|
| | | 3-6 | 3-7 | 3-8 | 3-9 |
| A and B | SL-containing Composition 2 | 0.02 | 0.1 | 0.5 | 0.58 |
| | (A: Acidic SL) | (0.01996) | (0.0998) | (0.499) | (0.579) |
| | (B: Free Fatty Acid) | (0.00004) | (0.0002) | (0.001) | (0.00116) |
| B | Oleic Acid | 0 | 0 | 0 | 0 |
| C | Sodium Hydrogen Carbonate | 0 | 0 | 0 | 0 |
| Water (Hardness: 100 mg/L) | | Remainder | Remainder | Remainder | Remainder |
| Total Amount | | 100 | 100 | 100 | 100 |
| Total Free Fatty Acid Concentration in Water/% | | 0.00004 | 0.0002 | 0.001 | 0.00116 |
| Generated Gas | | None | None | None | None |
| Evaluation of UFB | Scattering Intensity | C | C | C | C |
| | Average Number Particle Size | C | C | C | C |

TABLE 4-continued

| Formulas of Comparative Test Samples and Evaluation Results | | | | |
|---|---|---|---|---|
| Evaluation Result of Removal Effect | A | AA | AA | AA |
| Cell Viability/% (L929 cell 48 h) | — | 83.1 | 16.8 | 12.4 |
| (Evaluation Result) | | (AA) | (C) | (C) |
| Cell Viability/% (V79 cell 48 h) | — | 82.3 | 61.1 | 59.3 |
| (Evaluation Result) | | (AA) | (A) | (A) |

—: Not Measured

These comparative test samples were subjected to UFB evaluation, biofilm removal effect evaluation, and safety evaluation in the same manner as in Experimental Examples 1 to 3 above. Tables 3 and 4 collectively show the results. As shown in Table 3, although $CO_2$ gas was generated without adding components A and B to component C, no ultrafine bubbles formed and no biofilm removal effect was observed (Comparison Test Samples 1-1 to 1-6). Additionally, as shown in Tables 3 and 4, no $CO_2$ gas (UFBs) was generated with component B alone or with components A and B alone (Comparative Test Samples 2-1 to 2-3 and 3-1 to 3-9). However, as shown in Table 4, using acidic SL at a concentration of 0.01996% or higher in an aqueous solution was confirmed to be effective in removing biofilms, although $CO_2$ gas (UFBs) was not produced (Comparative Test Samples 3-6 to 3-9). However, it was also confirmed that using acidic SL at a concentration as high as 0.4% or higher reduced cell viability, decreasing safety (Comparative Test Samples 3-8 and 3-9).

Experimental Example 5: Experimental Evaluation of Biofilm Removal Effect Using Pig Skin Model A biofilm removal effect on a pig skin model (biofilm model) was evaluated by using Test Sample 1-2, which was confirmed to show UFB generation, a biofilm removal effect, and safety in Experimental Examples 1 to 3, according to the following method.

(1) Experimental Method: Preparation of Pig Skin Model

An about 1-mm-deep depression was made in a 5-cm square of pig skin with a thickness of several millimeters to 1 cm (obtained from Tokyo Shibaura Zoki) with a biopsy trepan and scissors.

Thereafter, the pig skin was disinfected with an aqueous solution of sodium hypochlorite.

The pig skin having the surface disinfected was inoculated with 20 μL of a test solution of bacteria.

Assuming actual wound treatment, an adhesive bandage (Careleaves: Nichiban Co., Ltd.) was applied to the inoculation site. After the adhesive bandage was applied, culture was performed at 37° C. for 24 hours.

The thus-prepared pig skin was used as a model (biofilm model).

Test Solution of Bacteria

The test solution of bacteria used above was prepared as follows.

A test solution of *P. aeruginosa* (PAO-1) cultured at 37° C. for 72 hours in a TSA medium was suspended in physiological saline to prepare a bacteria solution of about $10^q$ to $10^9$ CFU/mL.

The bacterial solution was diluted stepwise with physiological saline to $10^5$ to $10^6$ CFU/mL.

Experimental Method

The pig skin model was sprayed with a biofilm removal solution (Test Sample 1-2) in an atomizer (electric atomizer: Tovia Tools Co., Ltd.) at a rate of 6 mL/cm$^2$ (spraying only, no washing with water). The biofilm removal solution was prepared by adding a powdered SL-containing composition and sodium hydrogen carbonate to an atomizer containing tap water (hardness of 100 mg/L, room temperature) to reach a predetermined concentration, then covering the atomizer and shaking it for about 10 seconds. Immediately after spraying, the spray-treated pig skin model was stained with a biofilm detection tool (Saraya Co., Ltd.) according to the instructions for the detection tool, and the residual biofilm was visually evaluated based on the degree of staining.

(2) Experimental Results

FIG. 1 shows the results. In FIG. 1, A illustrates the results of an unwashed pig skin model, B illustrates a pig skin model washed with tap water (hardness of 100 mg/L, room temperature), and C illustrates the pig skin model sprayed with a biofilm removal solution (Test Sample 1-2). Darker areas in light blue indicate the residual biofilm. As shown in FIG. 1, although the biofilm on the skin surface could not be removed simply by washing with water, spray treatment with the biofilm removal solution of the present invention was confirmed to be able to remove biofilms effectively.

Experimental Example 6: Preparation of Biofilm Remover and Biofilm Removal Solution ($H_2$ Gas Generation), and Evaluation of Biofilm Remover and Biofilm Removal Solution SL-containing composition 2, oleic acid, and magnesium hydride ($H_2$ gas generator) were added to tap water (hardness of 100 mg/L, room temperature) in a glass beaker to give the concentrations listed in Table 5, and stirred with a stirring bar and an agitator to dissolve them, thereby preparing a biofilm removal solution (Test Samples 4-1 to 4-6 with a pH of 8 to 11). The prepared biofilm removal solutions were evaluated for UFB formation, a biofilm removal effect, and safety according to the methods described in Experimental Examples 1 to 3. For comparison, biofilm removal solutions of comparative formula 4 (Comparative Test Samples 4-1 and 4-2) were prepared and also evaluated for UFB formation, a biofilm removal effect, and safety in the same manner.

Table 5 shows the percentage (%) of each component in the biofilm removal solutions and evaluation results.

TABLE 5

Biofilm Removal Solution and Evaluation Results

Mass %

| | | Test Sample Formula 4 | | | |
|---|---|---|---|---|---|
| | | 4-1 | 4-2 | 4-3 | 4-4 |
| A and B | SL-containing Composition 2 | 0.0001 | 0.001 | 0.01 | 0.002 |
| | (A: Acidic SL) | (0.0000998) | (0.000998) | (0.00998) | (0.001996) |
| | (B: Free Fatty Acid) | (0.0000002) | (0.000002) | (0.00002) | (0.000004) |
| B | Oleic Acid | 0.00001 | 0.0001 | 0.001 | 0.0002 |
| C | Magnesium Hydride | 0.001 | 0.001 | 0.01 | 0.02 |
| Water (Hardness: 100 mg/L) | | Remainder | Remainder | Remainder | Remainder |
| Total Amount | | 100 | 100 | 100 | 100 |
| Total Free Fatty Acid Concentration in Water/% | | 0.0000102 | 0.000102 | 0.00102 | 0.000204 |
| Generated Gas | | $H_2$ | $H_2$ | $H_2$ | $H_2$ |
| Evaluation of UFB | Scattering Intensity | C | A | — | — |
| | Average Number Particle Size | C | AA | — | — |
| Evaluation Result of Removal Effect | | B | A | A | AA |
| Cell Viability/% (L929 cell 48 h) (Evaluation Result) | | >100 (AA) | >100 (AA) | >100 (AA) | >100 (AA) |
| Cell Viability/% (V79 cell 48 h) (Evaluation Result) | | >100 (AA) | >100 (AA) | >100 (AA) | >100 (AA) |

Mass %

| | | Test Sample | | | |
|---|---|---|---|---|---|
| | | Formula 4 | | Comparative Formula 4 | |
| | | 4-5 | 4-6 | 4-1 | 4-2 |
| A and B | SL-containing Composition 2 | 0.012 | 0.1 | 0 | 0 |
| | (A: Acidic SL) | (0.01198) | (0.0998) | | |
| | (B: Free Fatty Acid) | (0.00002) | (0.0002) | | |
| B | Oleic Acid | 0.0012 | 0.01 | 0 | 0 |
| C | Magnesium Hydride | 0.1 | 0.9 | 0.001 | 0.02 |
| Water (Hardness: 100 mg/L) | | Remainder | Remainder | Remainder | Remainder |
| Total Amount | | 100 | 100 | 100 | 100 |
| Total Free Fatty Acid Concentration in Water/% | | 0.00122 | 0.0102 | 0 | 0 |
| Generated Gas | | $H_2$ | $H_2$ | $H_2$ | $H_2$ |
| Evaluation of UFB | Scattering Intensity | — | — | C | C |
| | Average Number Particle Size | — | — | C | C |
| Evaluation Result of Removal Effect | | AA | AA | C | C |
| Cell Viability/% (L929 cell 48 h) (Evaluation Result) | | 50.1 (A) | — | >100 (AA) | >100 (AA) |
| Cell Viability/% (V79 cell 48 h) (Evaluation Result) | | 51.7 (A) | — | >100 (AA) | >100 (AA) |

—: Not Measured

As shown in Table 5, the biofilm removal solutions (Test Samples 4-1 to 4-6) all produced $H_2$ gas when all components were dissolved in water. All of the biofilm removal solutions were also confirmed to be effective in removing biofilms. In particular, 30% or more of biofilms were removed with Test Samples 4-3 to 4-6, as well as Test Sample 4-2, which was confirmed to form UFBs. In particular, Test Samples 4-4 to 4-6 were highly effective in removing biofilms. No UFB formation was observed in Test Sample 4-1. However, as shown in Test Sample 4-2, UFBs were formed when the SL content, fatty acid content, and magnesium hydride content in the biofilm removal solution were respectively about 0.001% or higher, about 0.0001% or higher, and about 0.001% or higher. This was also confirmed to increase the biofilm removal effect. Additionally, the cell viability of both types of cells exposed to every biofilm removal solution was confirmed to be as high as 50% or higher. In particular, the cell viability of the cells with Test Samples 4-1 to 4-4 was higher than that with physiological saline, indicating that the test samples are highly safe for living organisms.

In contrast, dissolving only magnesium hydride ($H_2$ gas generator component) in water produced $H_2$ gas, but not UFBs, and was also not effective in removing biofilms (Comparative Test Samples 4-1 and 4-2).

Experimental Example 7: Preparation of Biofilm Remover and Biofilm Removal Solution ($O_2$ Gas Generation), and Evaluation of Biofilm Remover and Biofilm Removal Solution SL-containing composition 2, oleic acid, hydrogen peroxide ($O_2$ gas generator), and catalase as its counterpart were added to tap water (hardness of 100 mg/L, room temperature) in a glass beaker to give the concentrations listed in Table, 6 and stirred with a stirring bar and an agitator to dissolve them, thereby preparing a biofilm removal solution (Test Samples 5-1 to 5-5 with a pH of 7 to 8). The prepared biofilm removal solutions were evaluated for UFB formation, a biofilm removal effect, and safety according to the methods described in Experimental Examples 1 to 3. For comparison, biofilm removal solutions of formula 5 (Comparative Test Samples 5-1 to 5-3) were prepared and also evaluated for UFB formation, a biofilm removal effect, and safety in the same manner.

Table 6 shows the percentage (%) of each component in the biofilm removal solutions and evaluation results.

TABLE 6

Biofilm Removal Solution and Evaluation Results

Mass %

| | | Test Sample | | | | | | | |
|---|---|---|---|---|---|---|---|---|---|
| | | Formula 5 | | | | | Comparative Formula 5 | | |
| | | 5-1 | 5-2 | 5-3 | 5-4 | 5-5 | 5-1 | 5-2 | 5-3 |
| A and B | SL-containing Composition 2 | 0.005 | 0.008 | 0.01 | 0.014 | 0.1 | 0 | 0 | 0 |
| | (A: Acidic SL) | (0.00499) | (0.007984) | (0.00998) | (0.013972) | (0.0998) | | | |
| | (B: Free Fatty Acid) | (0.00001) | (0.000016) | (0.00002) | (0.000028) | (0.0002) | | | |
| B | Oleic Acid | 0.0005 | 0.0008 | 0.001 | 0.0014 | 0.01 | 0 | 0 | 0 |
| C | Hydrogen Peroxide | 0.019 | 0.042 | 0.17 | 0.18 | 0.9 | 0.0042 | 0.019 | 0.18 |
| | Catalase | 0.011 | 0.024 | 0.1 | 0.14 | 0.4 | 0.0022 | 0.012 | 0.11 |
| Water (Hardness: 100 mg/L) | | Remainder | Remainder | Remainder | Remainder | Remainder | Remainder | Remainder | Remainder |
| Total Amount | | 100 | 100 | 100 | 100 | 100 | 100 | 100 | 100 |
| Total Free Fatty Acid Concentration in Water/% | | 0.00051 | 0.000816 | 0.00102 | 0.001428 | 0.0102 | 0 | 0 | 0 |
| Generated Gas | | $O_2$ | $O_2$ | $O_2$ | $O_2$ | $O_2$ | $O_2$ | $O_2$ | $O_2$ |
| Evaluation of UFB | Scattering Intensity | AA | — | AA | — | — | C | C | C |
| | Average Number Particle Size | B | — | A | — | — | C | C | C |
| Evaluation Result of Removal Effect | | A | A | A | A | A | C | C | C |
| Cell Viability/% (L929 cell 48 h) (Evaluation Result) | | >100 (AA) | >100 (AA) | >100 (AA) | >100 (AA) | 83.1 (AA) | >100 (AA) | >100 (AA) | >100 (AA) |
| Cell Viability/% (V79 cell 48 h) (Evaluation Result) | | >100 (AA) | >100 (AA) | >100 (AA) | >100 (AA) | 82.3 (AA) | >100 (AA) | >100 (AA) | >100 (AA) |

—: Not Measured

As shown in Table 6, each biofilm removal solution (Test Samples 5-1 to 5-5) produced $O_2$ gas when all components were dissolved in water. UFB formation was also observed. Furthermore, all of the biofilm removal solutions were confirmed to be effective in removing 30% or more of biofilms. The cell viability of both types of cells exposed to every biofilm removal solution was confirmed to be as high as 80% or higher, which was higher than that with physiological saline, indicating that the test samples are highly safe for living organisms.

In contrast, dissolving only hydrogen peroxide ($O_2$ gas generator) and its counterpart, catalase, in water produced $O_2$ gas, but not UFBs, and was also not effective in removing biofilms (Comparative Test Samples 5-1 to 5-3).

The invention claimed is:

1. A biofilm remover comprising a combination of the following (A), (B), and (C):

(A) a sophorolipid containing acidic sophorolipid and lactonic sophorolipid in a mass ratio of 78:22 to 100:0;

(B) a free fatty acid or a salt thereof; and (C) a gas generation component, wherein ultrafine bubbles are generated by adding (A), (B), and (C) to water such that (A), (B), and (C) coexist in the water, and wherein the ultrafine bubbles have an average number particle size of 50 nm or more and less than 1000 nm as measured with a dynamic light scattering spectrophotometer.

2. The biofilm remover according to claim 1, wherein (C) is at least one member selected from the group consisting of a carbon dioxide gas generation component, a hydrogen gas generation component, and an oxygen gas generation component.

3. The biofilm remover according to claim 2, wherein the carbon dioxide gas generation component is a carbonate or a hydrogen carbonate, or a combination of a carbonate or a hydrogen carbonate with a counterpart corresponding thereto;

the hydrogen gas generation component is a hydride, a borohydride, or hydrochloric acid, or a combination of a hydride, a borohydride, or hydrochloric acid with a counterpart corresponding thereto; and the oxygen gas generation component is hydrogen peroxide or a combination of hydrogen peroxide with a counterpart corresponding thereto.

4. The biofilm remover according to claim 1, which is a composition of (A), (B), and (C) or a product combination in which at least (C) is packaged separately from (A) and (B).

5. The biofilm remover according to claim 4, further comprising (D) water with a hardness of 30 to 200 mg/L in addition to (A), (B), and (C), wherein at least (D) is packaged separately from the composition of (A), (B), and (C) or from the product combination in which (C) is packaged separately from (A) and (B).

6. The biofilm remover according to claim 2, which is a composition of (A), (B), and (C) or a product combination in which at least (C) is packaged separately from (A) and (B).

7. The biofilm remover according to claim 6, further comprising (D) water with a hardness of 30 to 200 mg/L in addition to (A), (B), and (C), wherein at least (D) is packaged separately from the composition of (A), (B), and (C) or from the product combination in which (C) is packaged separately from (A) and (B).

* * * * *